United States Patent [19]

Gyorkos et al.

[11] Patent Number: 6,159,938
[45] Date of Patent: *Dec. 12, 2000

[54] SERINE PROTEASE INHIBITORS COMPRISING α-KETO HETEROCYCLES

[75] Inventors: Albert C. Gyorkos, Westminster; Lyle W. Spruce, Arvada; Axel H. Leimer, Lakewood; John C. Cheronis, Conifer, all of Colo.

[73] Assignee: Cortech, Inc.

[*] Notice: This patent is subject to a terminal disclaimer.

[21] Appl. No.: 08/859,242

[22] Filed: May 20, 1997

Related U.S. Application Data

[63] Continuation-in-part of application No. 08/761,190, Dec. 6, 1996, Pat. No. 5,807,829, which is a continuation-in-part of application No. 08/345,820, Nov. 21, 1994, Pat. No. 5,618,792.

[51] Int. Cl.$^7$ .......................... A61K 38/05; A61K 38/06; A61K 38/07; A61K 38/08
[52] U.S. Cl. .............................. 514/17; 435/1.1; 514/18; 514/19; 514/20; 514/361; 514/362; 514/363; 514/364; 514/383; 530/330; 530/331; 530/332; 548/128; 548/131; 548/136; 548/143; 548/266.8; 548/268.2
[58] Field of Search .................................. 514/17, 18, 19, 514/20, 361, 362, 363, 364, 383; 530/330, 331, 332; 435/1.1, 1.2, 1.3, 23, 213, 214, 217, 218, 219, 226; 548/128, 131, 136, 143, 266.8, 268.2

[56] References Cited

U.S. PATENT DOCUMENTS

| | | | |
|---|---|---|---|
| 4,338,453 | 7/1982 | Gall | 548/263 |
| 5,055,450 | 10/1991 | Edwards et al. | 514/19 |
| 5,164,371 | 11/1992 | Edwards et al. | 514/18 |
| 5,550,139 | 8/1996 | Groutas | 514/362 |
| 5,618,792 | 4/1997 | Gyorkos et al. | 514/18 |
| 5,801,148 | 9/1998 | Gyorkos et al. | 514/18 |
| 5,807,829 | 9/1998 | Gyorkos | 514/18 |
| 5,861,380 | 1/1999 | Gyorkos et al. | 514/19 |

FOREIGN PATENT DOCUMENTS

| | | | |
|---|---|---|---|
| 0 291 234 | 1/1988 | European Pat. Off. | C07K 5/06 |
| 376012 | 7/1990 | European Pat. Off. | |
| 0 480 044 | 4/1992 | European Pat. Off. | C07D 413/12 |
| 0 529 568 A1 | 3/1993 | European Pat. Off. | C07D 5/08 |
| 0 528 633 A1 | 3/1999 | European Pat. Off. | C07D 239/46 |
| 2 694 295 | 2/1994 | France | C07K 5/12 |
| 2224338 | 11/1972 | Germany | C07D 85/52 |
| 1397073 | 6/1975 | United Kingdom | C07D 271/06 |
| WO 93 21212 | 10/1993 | WIPO | C07K 5/06 |
| WO 95 33762 | 12/1995 | WIPO | C07K 5/06 |
| WO 96/16080 | 5/1996 | WIPO | C07K 5/062 |

OTHER PUBLICATIONS

Skiles, J.W., et al. "Elastase Inhibitors Containing Conformationally Restricted Lactams as P$_3$–P$_2$ Dipeptide Replacements," Bio. & Med. Chem. Ltrs. 3, 773–778 (1993).

Edwards, P. D., et al. "Peptidyl Alpha–Ketoheterocyclic Inhibitors of Human Neutrophil Elastase. 3. In Vitro and In Vivo Potency of a Series of Peptidyl Alpha–Ketobenzoxazoles," J. Med. Chem. 38, 3972–3982 (1995).

Edwards, P. D., et al. "Nonpeptic Inhibitors of Human Neutrophil Elastase. 7. Design, Synthesis, and in Vitro Acitivity of a Series of Pyridopyrimidine Trifluoromethyl Ketones," J. Med. Chem. 39, 1112–1124 (1996).

Edwards, P. D. et al. "Peptidyl Alpha–Ketoheterocyclic Inhibitors of Human Neutrophil Elastase. 2. Effect of Varying the Heterocyclic Ring on in Vitro Potency," J. Med Chem. 38, 76–85 (1995).

Veale, C. A., et al. "Non–peptidic Inhibitors of Human Leukocyte Elastase. 4. Design, Synthesis, and in Vitro and in Vivo Activity of a Series of Beta–Carbolinone–Containing Trifluoromethyl Ketones," J. Med. Chem. 38, 86–97 (1995).

Veale, C. A. et al. "Nonpeptidic Inhibitors of Human Leukocyte Elastase. 5. Design, Synthesis, and X–ray Crystallography of a Series of Orally Active 5–Aminopyrimidin–6–one–Containing Trifluoromethyl Ketones," J. Med. Chem. 38, 98–108 (1995).

Goddard, C. J., "Antiinflammatory 1–Phenylpyrazole–4–Heteroarylalkanoic Acids," J. Heterocyclics Chem., 28, 1607–1612 (1991).

LaMattina, J. L., et al. "Utility of 24 p–Nitrophenyl 3–Bromo–2,2–diethoxypropionate (NPBDP) in Heterocyclic Synthesis," J. Org. Chem. 49, 4800–4805 (1984).

Unangst, P.C., et al. "Novel 1,2,4–Oxadiazoles and 1,2,4–Thiadiazoles as Dual 5–Lipoxygenase and Cyclooxygenase Inhibitors," J. Med. Chem. 35, 3691–3698 (1992).

Kitatini, K., et al. "A Novel Oxazole Synthesis Utilizing Tungsten(VI) Catalyzed Decomposition of Alpha–Diazo Carbonyl Compounds in Nitriles," Tet. Lett. 16 1531–1532 (1974).

Wiley, R. H., "Chemistry of the Oxazoles," Chem. Rev. 37, 401–442 (1945).

Davidson, D., et al. "The Action of Ammonia of Bonzoin," J. Org. Chem. 2, 328–334 (1937).

Wiegand, Edwin E., et al. "Polyphosphoric Acid Cyclization of Acetamidoketones to 2,5–Dimethyl–1,3–oxazoles," Synthesis 12, 648–649 (1970).

Wasserman, H.H., et al. "The Oxazole–Triamide Rearrangement. Application To Peptide Synthesis," Tet. Lett. vol. 24, No. 37, 3831–3834 (1982).

(List continued on next page.)

*Primary Examiner*—Jeffrey E. Russel
*Attorney, Agent, or Firm*—Dechert

[57] ABSTRACT

Provided are methods of inhibiting the activity of a serine protease using protease inhibitors that include an alpha-keto heterocycle in their structure. The methods are useful in the treatment of ischemic heart or treatment of symptoms associated with blood coagulation disorders. Also provided are methods for detecting or quantifying the activity of a serine protease in a pure sample.

77 Claims, No Drawings

OTHER PUBLICATIONS

Comforth, J. W., et al. "A New Synthesis of Oxazoles and Iminazoles including its Application to the Preparation of Oxazole." J. Chem. Soc. 96–102 (1947).

Comforth, J. W., "Synthesis of Oxazoles from Ethyl Acetoacetate. Ring-fisson of Some Oxazole-5-carboxylic Acids." J. Chem Soc. 93–98 (1953).

Bernstein, P. R., et al. "Nonpeptidic Inhibitors of Human Leukocyte Elastase. 3. Design, Synthesis, X-Ray Crystallographic Analysis, and Structure—Activity Relationships for a Series of Orally Active 3-Amino-6-phenylpyridin-2-one Trifluoromethyl Ketones," J. Med. Chem. 37, 3313–3326 (1994).

Brown, F. J., et al. "Design of Orally Active, Non–Peptidic Inhibitors of Human Leukocyte Elastase," J. Med. Chem. 37, 1259–1261 (1994).

Warner, P., et al. "Non–peptidic Inhibitors of Human Leukocyte Elastase. 1. The Design and Synthesis of Pyridone–Containing Inhibitors," J. Med. Chem. 37, 3090–3099 (1994).

Budavari, Susan (Editor), "The Merck Index," An Encylopedia of Chemicals, Drugs, and Biologicals; Merck & Co., Inc., p. 294 (1989).

Damewood, J. R., et al. "Nonpeptidic Inhibitors of Human Leukocyte Elastase. 2. Design, Synthesis, and in vitro Activity of a Series of 3-Amino-6-arylopyridin-2-one Trifluoromethyl Ketones," J. Med. Chem. 37, 3303–3312 (1994).

SERINE PROTEASE INHIBITORS COMPRISING α-KETO HETEROCYCLES

This application is a continuation-in-part of U.S. Ser. No. 08/761,190 filed Dec. 6, 1996 now U.S. Pat. No. 5,807,829; which is a continuation-in-part of U.S. Ser. No. 08/345,820 filed Nov. 21, 1994 now U.S. Pat. No. 5,618,792.

BACKGROUND OF THE INVENTION

The serine proteases are a class of enzymes which includes elastase, proteinase 3, chymotrypsin, cathepsin G, trypsin, thrombin, prolyl oligopeptidase and others. A breakdown in the balance of protease/antiprotease activity has been implicated in the pathogenesis of numerous disease states.

For example, it is known that many human malignancies are associated with enhanced expression of proteases (Opdenakker et al., Cytokine, 4:251–258 (1992)). These proteases may be involved in growth, chemotaxis, endocytosis, exocytosis, blood coagulation, fibrinolysis and tissue invasion during metastasis of malignant cells (Eisenbrand. Synthesis, 1246–1252 (1996); Kazama, J.B.C. 270:66–72 (1995)). Specifically, plasmin, urokinase-plasminogen activator (uPA) and tissue plasminogen activator (tPA) and a tumor-associated trypsin show a substantial increase in activity in many malignancies.

Tumor-associated trypsin has been shown to participate in cancer cell-mediated degradation of extracellular matrix (Koivunen et al., Cancer Research, 51:2107–2112 (1991)) and has been implicated in tumor invasion. Human urinary trypsin inhibitors have been shown to prevent both the intravasation and extravasation step of tumor metastasis (Int. J. Cancer, 63:455–462 (1995)). Urokinase-plasminogen activator and tPA have also been shown to be important in tumor metastasis (Dowell, et al., Cancer Treatment Reviews, 19:283–296 (1993)). A guanidinobenzoatase has been implicated in cancer metastasis, cell migration and tissue remodeling (Poustis-Delpont C. et al., J.B.C., 269:14666–71 (1994); Stevens et al., Br. J. Cancer, 46:934–939 (1982); Ohkoshi et al., J. Max. Fac. Surg., 12:148–152 (1984); Poustis-Delpont et al., Cancer Research, 52:3622–3628 (1992); Stevens, Biol. Chem., 69:137–143 (1988)).

Increased plasmin activity has been directly correlated to increased plasminogen activator activity (Eisenbrand, Synthesis, 1246–1252 (1996)). Compounds capable of inhibiting plasmin, tumor-associated trypsin, guanidinobenzoatase or plasminogen activator represent potential drug candidates for the treatment of the various human malignancies.

Hepsin, a membrane associated serine protease, has been shown to activate human factor VII and to initiate a pathway of blood coagulation on the cell surface leading to thrombin formation (Kazama. J.B.C., 270:66–72 (1995)). It is believed that a variety of neoplastic cells activate the blood coagulation system, causing hypercoagulability and intravascular thrombosis via this and other pathways and that hepsin plays a role in their cell growth, maintenance and morphology (Torres-Rosada et al., Proc. Natl. Acad. Sci. USA, 90:7181–7185 (1993)). Hepsin is present at elevated levels in regions of active cell proliferation in animal models and anti-hepsin antibody has been shown to suppress the growth of human hepatoma cells in culture. Hepsin is also suspected to be a physiological inactivator of the tumor suppressor protein maspin.

Chymase is believed to be responsible for angiotensin I converting enzyme (ACE) independent activation of angiotensin II in the heart (Urata, et al., J.B.C., 265:2963–2968 (1997)). This event appears to play a role in the hypoxic or ischemic heart (Urata, et al., Am. J. Hyprtens., 9:277–284 (1996)). In addition, in the failing or compromised heart, human chymase is believed to be responsible for an alternate production of angiotensin II, which has been shown to take place in the presence of angiotensin converting enzyme (ACE) inhibitor.

A cause and effect relationship has been shown between endogenous vascular elastase (EVE) and experimentally induced pulmonary hypertension in experimental animal models (Zhu, et al., J. Clin. Invest., 94:1163–1171 (1994)). Pulmonary hypertension is commonly associated with congenital heart defects, pulmonary diseases associated with chronic hypoxia, hepatic disorders and connective tissue disease. Increased pulmonary artery elastolytic activity associated with the monocrotaline-induced pulmonary hypertension model has been shown to be moderated by treatment with an elastase inhibitor (Ye, et al., Am. J. Physiol. 261 (Heart Circ. Physiol. 30): H1255–H1267 (1991); Cowan et al., J. Clin Invest., 97:2452–2468 (1996)). In some models, early inhibition of EVE activity largely prevented pulmonary vascular damage. Although, EVE has been shown to be sensitive to leukocyte elastase (LE) inhibitors, it is believed that it is a novel enzyme distinct from LE. Inhibitors of EVE may be useful in treating pulmonary vascular disease in infants, restenosis secondary to angioplasty, pulmonary hypertension myocarditis, bronchopulmonary dysplasia, myocardial necrosis after cardiac transplant, post-cardiac transplant coronary arteriopathy, atherosclerosis and reperfusion injury following myocardial infarct.

Prolyl oligopeptidase degrades oxytocin, neurotensin, substance P, thyrotropin releasing hormone, bradykinin, angiotensin II and vasopressin (U.S. Pat. No. 5,506,256; Tsutsumi, et al., J. Med. Chem., 37:3492–3502 (1994)). It is also believed to degrade amyloid precursor protein, and therefore is suspected to play a role in Alzheimer's disease.

Aprotinin, a pancreatic basic trypsin inhibitor, was first described by H. Kraut et al. in 1930 (J. Physiol. Chem., 192:1 (1930)). Aprotinin has been studied and characterized extensively over the last few decades. It is the active ingredient of Trasylol® (Miles Laboratories), a drug which is marketed for the treatment of diseases such as hyperfibrinolytic hemorrhage and traumatic-hemorrhagic shock, or acute pancreatitis. Aprotinin has been shown to be an inhibitor of serine proteases (Fritz et al., Drug Res. 33 (1):479–494 (1983)), and is considered to be a broad-specificity inhibitor. In addition to trypsin and chymotrypsin, aprotinin inhibits plasmin and several kallikreins. It is also used prophylactically to reduce perioperative blood loss and to reduce the need for blood transfusions, mainly in patients undergoing coronary artery bypass graft surgery.

Although aprotinin is generally well tolerated, its main adverse side effects include increased incidence of postoperative renal dysfunction and allergic reactions, in some cases leading to anaphylaxis, which has in some cases been fatal. Patients who have had prior exposure to aprotinin are at higher risk for anaphylaxis. These two main adverse effects are both due to the properties of aprotinin as a protein, problems which may be overcome with a small, low molecular weight, synthetic drug with a similar inhibition profile as aprotinin. Additionally, new synthetic drugs would eliminate the need for extracting aprotinin from bovine lung or for its combinatorial expression.

It is clear that a need exists for methods of treating and/or preventing serine protease mediated pathologies.

SUMMARY OF THE INVENTION

The present invention provides methods of inhibiting the enzymatic activity of serine proteases comprising contacting such protease or proteases with an inhibitory amount of a compound of formula (I):

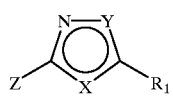

wherein Z is a serine protease binding moiety;

$R_1$ is alkyl or alkenyl optionally substituted with 1–3 halo or hydroxy; alkylamino, dialkylamino, alkyldialkylamino; or cycloalkyl, alkylcycloalkyl, alkenylcycloalkyl, $(C_5-C_{12})$aryl, $(C_5-C_{12})$arylalkyl or $(C_5-C_{12})$arylalkenyl optionally comprising 1–4 heteroatoms selected from N, O and S, and optionally substituted with halo, cyano, nitro, hydroxy, haloalkyl, amino, aminoalkyl, dialkylamino, alkyl, alkenyl, alkylenedioxy, alkynyl, alkoxy, haloalkoxy, carboxyl, carboalkoxy, alkylcarboxamide, $(C_5-C_6)$aryl, —O—$(C_5-C_6)$aryl, arylcarboxamide, alkylthio or haloalkylthio; and X and Y are independently O, S or N, said N being optionally substituted with alkyl or alkenyl optionally substituted with 1–3 halo atoms; $(C_5-C_6)$aryl, arylalkyl or arylalkenyl optionally comprising 1–3 heteroatoms selected from N, O and S, and optionally substituted with halo, cyano, nitro, hydroxy, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio;

wherein at least one of X or Y is N. It will be understood that where X or Y is substituted N, both X and Y are N.

In one embodiment, $R_1$ is methyl, dimethylamino, phenyl or benzyl optionally substituted with methyl, halo, methylenedioxy, methoxy, dimethoxy, trimethoxy, trifluoromethyl and dimethylamino.

According to several preferred embodiments, X is O and Y is N; X is N and Y is O; or both X and Y are N.

In a preferred embodiment, Z is of the formula (II):

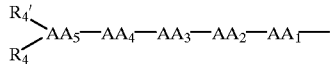

wherein $AA_1$, $AA_2$, $AA_3$, $AA_4$ and $AA_5$ are independently an amino acid residue or amino acid residue mimetic; a direct bond or absent; and $R_4$ and $R_4'$ are independently —C(O)$R_5$, —C(O)NH$R_5$, —S(O)$_2R_5$, —C(O)O$R_5$, —C(O)—$(C_5-C_6)$aryl-C(O)—$R_5$, —C$R_5$ or $R_5$, where $R_5$ is H, alkyl, alkenyl or alkynyl optionally substituted with halo, cyano, nitro, hydroxy, alkoxy, haloalkyl, amino, aminoalkyl, dialkylamino, haloalkoxy, carboxyl, carboalkoxy or alkylcarboxamide; cycloalkyl, alkylcycloalkyl, $(C_5-C_{12})$aryl or $(C_5-C_{12})$arylalkyl optionally comprising 1–4 heteroatoms selected from N, O and S, and optionally substituted with halo, cyano, nitro, hydroxy, alkoxy, haloalkyl, amino, aminoalkyl, dialkylamino, haloalkoxy, carboxyl, carboalkoxy, alkylcarboxamide, alkyl, alkenyl, alkynyl or $(C_5-C_{12})$aryl; or absent; or together $R_4$ and $R_4'$ form a ring comprising 5–7 atoms selected from C, N, S and O.

Thus, preferably, Z comprises a pentapeptidyl, tetrapeptidyl tripeptidyl or dipeptidyl binding moiety.

Preferably, the amino acids are selected from arginine or an arginine mimetic, proline; aspartic and glutamic acid and the aryl and alkyl esters thereof, alanine and glycine optionally substituted at the α-carbon or α-nitrogen with alkyl, cycloalkyl or aryl; leucine, isoleucine; cysteine optionally substituted at the sulfur atom with alkyl, alkenyl or phenyl optionally substituted with halo, cyano, nitro, haloalkyl, amino, aminoalkyl, dialkylamino, alkyl, allsoxy, haloalkoxy, carboxyl, carboalkoxy, alkylcarboxamide, arylcarboxamide, alkylthio or haloalkylthio, phenylalanine, homo-phenylalanine, dehydro-phenylalanine, indoline-2-carboxylic acid; tetrahydroisoquinoline-2-carboxylic acid optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio, tyrosine, serine or threonine optionally substituted with alkyl or aryl; tryptophan, histidine, methionine, valine, norvaline, norleucine, octahydroindole-2-carboxylic acid; asparagine, glutamine, ornithine and lysine optionally substituted at the nitrogen atom with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S.

Alternatively, $AA_1$ may be described by the formula (IIIa):

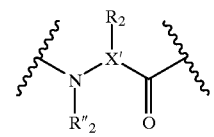

wherein X' is $CR_2'$ or N; and $R_2$, $R_2'$ and $R_2''$ are independently H; alkyl or alkenyl optionally substituted with 1–3 halo, hydroxy, thio, alkylthio, amino, alkylamino, dialkylamino, alkylguanidinyl, dialkylguanidinyl, guanidinyl or amidylguanidine; —RCOR', —RCOOR', —RNR'R"R° or —RC(O)NR'R" where R is alkyl or alkenyl, and R', R" and R° are independently H, alkyl, alkenyl, cycloalkyl or $(C_5-C_6)$aryl; or cycloalkyl, alkylcycloalkyl, alkenylcycloalkyl, alkyl-oxyaryl, alkyl-thioaryl, alkyl-aminoaryl, $(C_5-C_{12})$aryl, $(C_5-C_{12})$arylalkyl or $(C_5-C_{12})$arylalkenyl optionally comprising 1–4 heteroatoms selected from N, O and S, and optionally substituted with hydroxy, halo, cyano, keto, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, $(C_5-C_6)$aryl, —O—$(C_5-C_6)$aryl, arylcarboxamide, alkylthio or haloalkylthio; or $R_2$ and $R_2'$ together with X', where X' is C, form a ring comprising 4–7 atoms selected from C, N, S and O, said ring optionally substituted with hydroxy, halo, cyano, nitro, haloalkyl, amino, aminoalkyl, dialkylamino, amidine, alkylamidine, dialkyl amidine, alkyl, alkenyl, alkynyl, alkoxy, haloalkoxy, carboxyl, carboalkoxy, alkylcarboxamide, (C$_5$–C$_6$)aryl, —O-(C$_5$–C$_6$)aryl, arylcarboxamide, alkylthio or haloalkylthio.
Similarly, AA$_2$ may be described by the formula (IIIb):
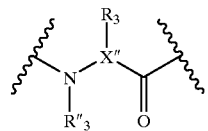
(IIIb)
or alternatively selected from a mimetic of formulas IV to XXIV:
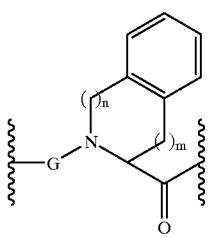
(IV)
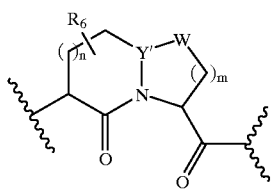
(V)
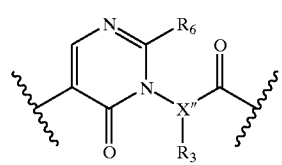
(VI)
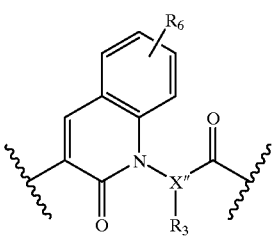
(VII)
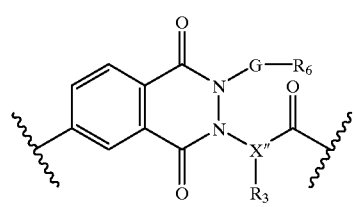
(VIII)
-continued
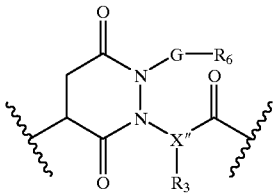
(IX)
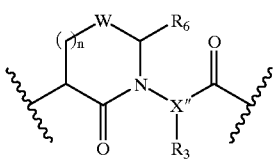
(X)
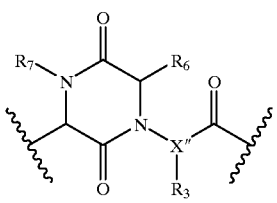
(XI)
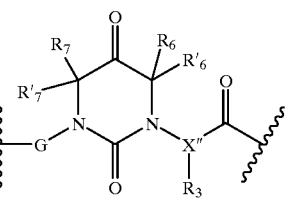
(XII)
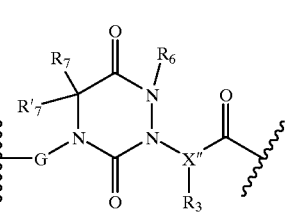
(XIII)
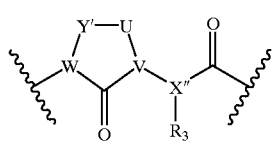
(XIV)
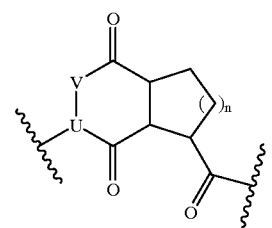
(XV)

(XVI)
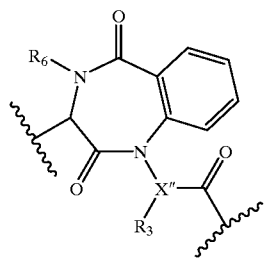

(XVII)
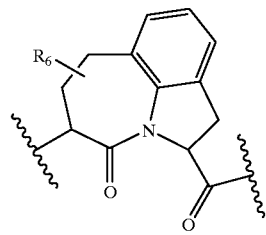

(XVIII)
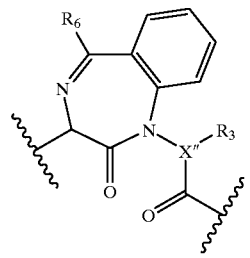

(XIX)
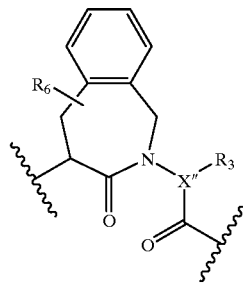

(XX)
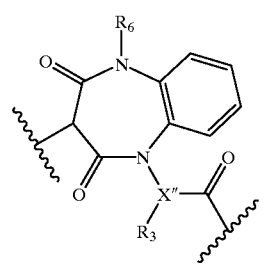

(XXI)
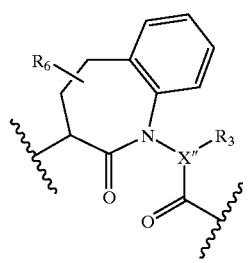

(XXII)
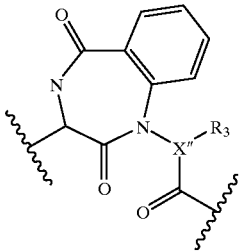

(XXIII)
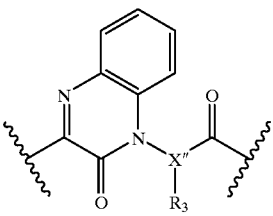

(XXIV)
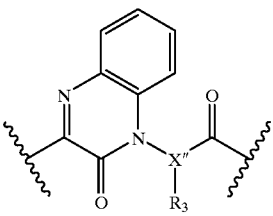

wherein X" is CR'$_3$ or N;

$R_3$, R'$_3$ and R"$_3$ are independently H; alkyl or alkenyl optionally substituted with 1–3 halo, hydroxy, thio, alkylthio, amino, alkylamino, dialkylamino, alkylguanidinyl, dialkylguanidinyl, guanidinyl or amidylguanidine; —RCOR', —RCOOR', —RNR'R"R° or —RC(O)NR'R" where R is alkyl or alkenyl, and R', R" and R° are independently H, alkyl, alkenyl, cycloalkyl or ($C_5$–$C_6$)aryl; or cycloalkyl, alkylcycloalkyl, alkenylcycloalkyl, alkyl-oxyaryl, alkyl-thioaryl, alkyl-aminoaryl, ($C_5$–$C_{12}$)aryl, ($C_5$–$C_{12}$)arylalkyl or ($C_5$–$C_{12}$)arylalkenyl optionally comprising 1–4 heteroatoms selected from N, O and S, and optionally substituted with hydroxy, halo, cyano, keto, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, ($C_5$–$C_6$)aryl, —O-($C_5$–$C_6$)aryl, arylcarboxamide, alkylthio or haloalkylthio;

m is 0, 1 or 2;

n is 0, 1 or 2;

G is —C(O)—, —NHC(O)—, —S(O)$_2$—, —OC(O)—, —C— or a direct bond;

$R_6$, $R_7$, R'$_6$, R'$_7$ are independently H, alkyl, alkenyl, halo, alkoxy, carboxyl, carboalkoxy, amino, aminoalkyl, dialkylamino; cycloalkyl, ($C_5$–$C_6$)aryl or ($C_5$–$C_6$) arylalkyl optionally comprising 1–3 heteroatoms selected from N, O and S, and optionally substituted with alkyl, alkenyl, alkynyl, halo, cyano, nitro, haloalkyl, hydroxy, amino, alkylamino, dialkylamino, alkoxy, haloalkoxy, carboxyl, carboalkoxy, alkylcarboxamide, alkylthio, guanidine, alkylguanidine, dialkylguanidine, amidine, alkylamidine or dialkylamidine; and U, V, W and Y' are independently or together N, C, C(O), N(R$_9$) where R$_9$, is H, alkyl, halo, alkoxy, carboalkoxy, cycloalkoxy, carboxyl, alkylthio, amino, alkylamino, dialkylamino, or aryl, fused aryl or cycloalkyl optionally comprising 1 or more heteroatoms selected from O, S and N, and optionally substituted with halo or alkyl; N(R$_{10}$) where R$_{10}$ is H, alkyl, alkenyl or cycloalkyl, aryl, arylalkyl or fused aryl-cycloalkyl optionally comprising 1–4 heteroatoms selected from N, O and S, and optionally substituted with alkyl, alkenyl, alkynyl, halo, cyano, nitro, haloalkyl, hydroxy, amino, alkylamino, dialkylamino, alkoxy, haloalkoxy, carboxyl, carboalkoxy, alkylcarboxamide, alkylthio, guanidine, alkylguanidine, dialkylguanidine, amidine, alkylamidine or dialkylamidine; or C(R$_{11}$)(R$_{12}$) where R$_{11}$ and R$_{12}$ are independently or together H, alkyl, alkylthio, alkylthioalkyl or cycloalkyl, alkylcycloalkyl, phenyl or phenvl alkyl optionally substituted with guanidine, carboalkoxy, hydroxy, haloalkyl, alkylthio, alkylguanidine, dialkylguanidine, amidine, alkylamidine or dialkylamidine.

AA$_3$, AA$_4$ and AA$_5$ may be either a direct bond or absent; or, where an amino acid, preferably selected from arginine or an arginine mimetic; proline; aspartic and glutanic acid and the aryl and alkyl esters thereof; alanine or glycine optionally substituted at the α-carbon or α-nitrogen with alkyl, cycloalkyl or aryl; leucine, isoleucine; cysteine optionally substituted at the sulfur atom with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homo-phenylalanine, dehydro-phenylalanine, indoline-2-carboxylic acid; tetrahydroisoquinoline-2-carboxylic acid optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; tyrosine, serine or threonine optionally substituted with alkyl or aryl; tryptophan, histidine, methionine, valine, norvaline, norleucine, octahydroindole-2-carboxylic acid; asparagine, glutamine, ornithine and lysine optionally substituted at the nitrogen atom with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S;

According to one embodiment, X' is N. In another embodiment, X" is N. Preferably, X' is CR'$_2$ and X" is CR'$_3$, where R'$_2$ and R'$_3$ are H.

Where the present method is used to inhibit thrombin, preferably AA$_1$ is Arg or an Arg mimetic. In one embodiment, X' is CR'$_2$ and R$_2$ is alkyl or alkenyl substituted with guanidinyl, amino or amidylguanidine; benzyl optionally substituted with amidine; alkylpyridine, alkylamino pyridine; alkylimidazole or alkylaminoimidazole substituted with amino; or alkylcyclohexane, said hexane ring optionally comprising 1 or more nitrogen atoms and optionally substituted with 1 or more keto and/or amidine groups. More specifically, according to this embodiment, R$_2$ is —CH$_2$(CH$_2$)$_2$NHC(=NH)NH$_2$; —CH$_2$(CH$_2$)$_4$NH$_2$; benzylamidine; —CH$_2$(CH$_2$)$_2$NH-pyridine; —CH$_2$NHC(O)NHC(=NH)NH$_2$; —CH$_2$CH$_2$CH$_2$-(imidazole)-NH$_2$; —CH$_2$CH$_2$NH-(imidazole)-NH$_2$; or —CH$_2$-(N,N-diketocyclohexane)-C(=NH)NH$_2$; or alternatively represented by the following:

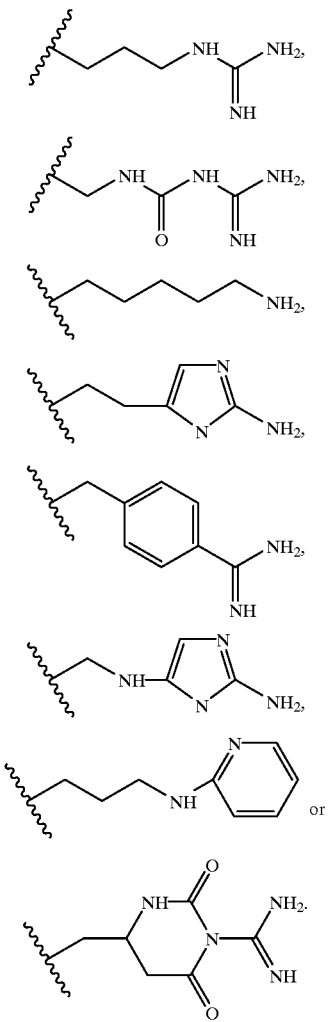

In one preferred embodiment, AA$_2$ is Gly.

Where the target serine protease is plasmin, preferably AA$_1$ is Arg or Arg mimetic; Lys or Orn; and more preferably Lys. In a further preferred embodiment, Z is R$_4$-Pro-Phe-AA$_1$-.

Where the serine protease is trypsin, preferably AA$_1$ is Arg or Lys.

In one embodiment, the serine protease is plasma kallikrein, where preferably Z is R$_4$-AA$_3$-AA$_2$-AA$_1$-; where AA$_1$ is Arg, Arg mimetic or Lys; AA$_2$ is Phe, Met or Leu; and AA$_3$ is Pro.

In another embodiment, the serine protease is tissue kallikrein, and preferably Z is R$_4$-AA$_4$-AA$_3$-AA$_2$-AA$_1$-; where AA$_1$ is Arg or Arg mimetic; AA$_2$ is Leu or Phe; AA$_3$ is Arg, Arg mimetic or Pro; and AA$_4$ is Thr. In certain species of this embodiment, Z is one of SEQ. ID NO:1 through SEQ. ID NO:12.

The methods of the present invention may also be used to inhibit the protease guanidinobenzoatase, where preferably AA$_1$ is Arg or Arg mimetic; or a guanidinobenzoyl containing moiety.

In addition, the methods may be used to inhibit chymase, where preferably Z is R$_4$-AA$_5$-AA$_4$-AA$_3$-AA$_2$-AA$_1$-; where AA$_1$ is Tyr, Phe, Trp or Leu. In a preferred embodiment, AA$_2$ is Pro; AA$_3$ is His; AA$_4$ is Ile; and AA$_5$ is Tyr (SEQ ID NO:13 through SEQ ID NO:16) Alternatively, AA$_2$ is a mimetic of formulas IV to XXIV (SEQ ID NO:17).

Where the serine protease is mast cell tryptase, preferably Z is $R_4$-$AA_3$-$AA_2$-$AA_1$-; where $AA_1$ is Arg or Arg mimetic; $AA_2$ is Gly, Val, Arg, Arg mimetic, Leu or Phe; and $AA_3$ is Leu, Arg, Arg mimetic, Lys, Ser or Phe.

Where the serine protease is prolyl oligopeptidase, preferably $AA_1$ is Pro.

In addition, the methods may be used to inhibit viral serine proteases such as hepatitis C virus NS3 polyprotein endopeptidase, where Z is preferably $R_4$-$AA_4$-$AA_3$-$AA_2$-$AA_1$-; where $AA_1$ is Cys; $AA_2$ is Cys or Ala; $AA_3$ is Val; and $AA_4$ is Val (SEQ ID NO:18 and SEQ ID NO:19).

Where the serine protease is human cytomegalovirus protease, preferably Z is $R_4$-$AA_4$-$AA_3$-$AA_2$-$AA_1$-; where $AA_1$ is Ala; $AA_2$ is Asn, Asp, Gln, Glu or Lys, or selected from their derivatives or esters; $AA_3$ is Val, Ile or Leu; and $AA_4$ is Val (SEQ ID NO:20 through SEQ ID NO:37).

The methods may also be used to inhibit assemblins, where preferably Z is $R_4$-$AA_4$-$AA_3$-$AA_2$-$AA_1$-; where $AA_1$ is Ala; $AA_3$ is Leu, Val or Ile; and $AA_4$ is Tyr; and preferably $AA_2$ is Gln or Lys, or their derivatives SEQ ID NO:38 through SEQ ID NO:46.

Where the serine protease is u-plasminogen activator, preferably Z is $R_4$-$AA_4$-$AA_3$-$AA_2$-$AA_1$; where $AA_1$ is Arg, Arg mimetic or Lys, $AA_2$ is Arg or Arg mimetic, Lys or a derivative thereof, or Gly; and $AA_3$ is Ser; and preferably $AA_4$ is Gly. Certain embodiments include SEQ ID NO:47 through SEQ ID NO:58.

Where the serine protease is t-plasminogen activator, Z is preferably $R_4$-$AA_3$-$AA_2$-$AA_1$-; where $AA_1$ Arg, Arg mimetic or Lys; $AA_2$ is Arg or Arg mimetic, Lys or a derivative thereof, Gly or Ala; and $AA_3$ is Arg or Arg mimetic.

The methods may also be used to inhibit Schistosoma serine proteases.

The present invention further provides the following novel inhibitors:

N-[N-(4-phenyl-1-ketobutane)-(L)-prolyl]-2-(S)-[(3-(3-phenylpropane)-1,2,4-oxadiazolyl)-ketomethane]-pyrrolidine (CQ-0006);

N-(Benzyloxycarbonyl)-L-valyl-N-[1-[3-[5-(2,6-difluorobenzyl)-1,2,4-oxadiazolyl]carbonyl]-2-(S)-methylpropyl]-L-prolinamide (CE-2036);

N-(Benzyloxycarbonyl)-L-valyl-N-[1-[3-[5-(3-trifluoromethylbenzyl)-1,2,4-oxadiazolyl]carbonyl]-2-(S)-methylpropyl]-L-prolinamide (CE-2048);

N-(Benzyloxycarbonyl)-L-valyl-N-[1-[3-[5-(3-trifluoromethylbenzyl)-1,2,4-oxadiazolyl]carbonyl]-2-(S)-methylpropyl]-N-benzylglycinamide (CE-2056);

N-Succinyl-L-valyl-N-[1-[3-[5-(3-trifluoromethylbenzyl)-1,2,4-oxadiazolyl]carbonyl]-2-phenylethylenyl]-L-prolinamide (CE-2061);

N-[4-(4-Morpholinocarbonyl)benzoyl]-L-valyl-N-[1-[3-[5-(3-trifluoromethylbenzyl)-1,2,4-oxadiazolyl]carbonyl]-2-(S)-methylpropyl]-L-prolinamide (CE-2064);

N-Acetyl-L-alanyl-N-[1-[3-[5-(3-trifluoromethylbenzyl)-1,2,4-oxadiazolyl]carbonyl]-2-(S)-methylpropyl]-L-prolinamide (CE-2081);

N-(Benzyloxycarbonyl)-L-valyl-N-[1-[2-[5-(3-methylbenzyl)-1,3,4-oxadiazolyl]carbonyl]-1-methylethyl]-L-prolinamide (CE-2083);

N-(Benzyloxycarbonyl)-L-t-butyltglycyl-N-[1-[3-[5-(3-trifluoromethylbenzyl)-1,2,4-oxadiazolyl]carbonyl]-2-methylpropyl]-L-prolinamide (CE-2093);

N-(Benzyloxycarbonyl)-L-Valyl-N-[1-[3-[5-(naphthyl-2-methylene)-1,2,4-oxadiazolyl]carbonyl]-2-(S)-methylpropyl]-L-prolinamide (CE-2152);

N-(Benzyloxycarbonyl)-L-TIC-N-[1-[2-[5-(3-methylbenzyl)-1,3,4-oxadiazolyl]carbonyl]-2-Methylpropyl]-L-prolinamide (CE-2183);

N-(3-Pyridylcarbonyl)-L-Valyl-N-[1-[3-[5-(3-methylbenzyl)-1,3,4-oxadiazolyl]carbonyl]-2-(S)-Methylpropyl]-L-prolinamide (CE-2161);

N-(Methanesulfonyl)-L-valyl-N-[1-[2-[5-(3-methylbenzyl)-1,3,4-oxadiazolyl]carbonyl]-2-(S)-methylpropyl]-L-prolinamide (CE-2163);

N-(Phenylsulfonyl)-L-valyl-N-[1-[2-[5-(3-methylbenzyl)-1,3,4-oxadiazolyl]carbonyl]-2-(S)-methylpropyl]-L-prolinanide (CE-2168);

N-(3-Pyridylcarbonyl)-L-valyl-N-[1-[3-[5-(3-trifluoromethylbenzyl)-1,2,4-oxadiazolyl]carbonyl]-2-(S)-methylpropyl]-L-prolinamide (CE-2171);

N-(4-Pyridylmethyleneoxycarbonyl)-L-valyl-N-[1-[3-[5-(3-trifluoromethylbenzyl)-1,2,4-oxadiazolyl]carbonyl]-2-(S)-methylpropyl]-L-prolinamide (CE-2185);

N-(4-Pyridylmethyleneoxycarbonyl)-L-valyl-N-[1-[2-[5-(3-methylbenzyl)-1,3,4-oxadiazolyl]carbonyl]-2-(S)-methylpropyl]-L-prolinainide (CE-2186); and N-(Pyrrolyl-2-carbonyl)-L-valyl-N-[1-[2-[5-(33-methylbenzyl)-1,3,4-oxadiazolyl]carbonyl]-2-(S)-methylpropyl]-N-(1-indanyl)glycinamide (CE-2195).

The compounds described herein may also be used as research and diagnostic tools, as coatings adsorbed or covalently attached to the surfaces of medical equipment and instruments such as bypass pumps, catheters and tubing, and as preservatives of transplantation tissues and organs.

As used herein, the term "serine protease binding moiety" means a chemical group capable of binding to the substrate binding site of a serine protease, typically defined in the literature as the $S_1$–$S_n$ site. The term includes both peptides and peptide mimetics. Preferably, the binding moiety is selected such that when linked to the keto-heterocycle, the moiety provides the resulting compound with inhibitory activity against the target serine protease of less than 100 µM ($K_i$ value); and more preferably of less than 10 µM.

As used herein, the term "optionally substituted" means, when substituted, mono to fully substituted.

As used herein, the term "independently" means that the substituents may be the same or different.

As used herein, the term "alkyl" means $C_1$–$C_{15}$, however, preferably $C_1$–$C_7$.

As used herein, the term "alkenyl" means $C_1$–$C_{15}$, however, preferably $C_1$–$C_7$.

As used herein, the term "alkynyl" means $C_1$–$C_{15}$, however, preferably $C_1$–$C_7$.

It will be understood that alkyl, alkenyl and alkynyl groups, whether substituted or unsubstituted, may be linear or branched.

As used herein, the term "aryl," unless otherwise stated, means aryl groups preferably comprising 5 to 12 carbons, and more preferably 5 to 6 carbons. Unless otherwise indicated, the term aryl includes mono- and bi-cyclic, as well as fused ring systems, including aryl-cylcoalkyl ring systems. As used herein, the tern "arylalkyl" includes mono-substituted alkyl groups (e.g., benzyl), as well as di-substituted alkyl groups such as -alkyl(phenyl)$_2$ (e.g., —CH(phenyl)$_2$). As used herein, where the term "arylalkyl" or "arylalkenyl" is defined by the general formula ($C_x$–$C_y$) arylalkyl or ($C_x$–$C_y$)arylalkenyl, x and y refer to the number of carbons making up the aryl group. The alkyl group is as defined above. As used here, the term "arylalkenyl" includes aryl compounds having an alkenyl chain comprising 1–3 or more double bonds, Exemplary arylalkenyl groups include =CH—CH$_2$-aryl and —CH=CH-aryl, where aryl is preferably phenyl.

As used herein, the term "arginine mimetic" means an amino acid residue with a side chain substituent of the formula —R'—C(=$^1$NH$_2$)NH$_2$; —R'—NHC(=$^1$NR")NR°; or —R'—NR"R° where R' is cycloalkyl, aryl or arylalkyl optionally substituted with one or more heteroatoms selected from N, S or O; and R" and R° are alkyl or cycloalkyl.

As used herein, the term "Cbz" means benzyloxycarbonyl; and the term "Mu" means morpholino.

Pharmaceutically acceptable salts of the compounds described above are within the scope of the invention.

DETAILED DESCRIPTION OF THE INVENTION

Peptidyl inhibitors of elastase comprising elastase binding moieties and certain keto-heterocycles have been previously described in the parent and grandparent applications of the present application (see also, WO 96/16080, incorporated herein). It has been surprisingly found that compounds comprising these keto-heterocycles are highly potent and specific inhibitors of a wide variety of other serine proteases as well. The inhibiting activity can be directed against any serine protease by identifying the binding moiety specific for that protease. The characteristics for the $P_1 \ldots P_n$ residues (using substrate nomenclature by Schechter and Berger (*Biochem. Biophys. Res. Commun.* 27: 157 (1967); *Biochem. Biophys. Res. Commun.* 32: 898 (1968)), which define the minimum recognition sequence of enzymes for small synthetic peptide substrates or inhibitors are known for many enzymes or can be determined by measuring rates of hydrolysis of various substrates.

For example, inhibitors may be designed based on the aprotinin binding profile, where the binding moieties may comprise Pro-Phe in the P3-P2 positions, and Arg or an Arg mimetic, Lys or Orn in the P1 position. For plasmin, Lys is preferred over Arg or its mimetic in the P1 position. Such inhibitors may be used to treat coagulation disorders.

Where the target protease is trypsin, Arg or an Arg mimetic is again preferred over Lys in the P1 position. Such inhibitors may be effective in treating, for example, pancreatitis.

Substrates of plasma kallikrein, which acts on kininogen to release kallidin and activates Factor XII, typically have Arg or Lys in the P1 position, although Arg is again preferred; bulky residues are preferred for P2, such as Phe, Met or Leu; and Pro is tolerated in P3 (Hibino et al., *J. Invest. Dermatol.* 90:505–510 (1988); Page et al., *J.B.C.* 266:8142–8148 (1991)).

Tissue kallikrein prefers Arg in P1; whereas bulky or negative residues are preferred in P2, such as Leu and Phe; Arg or Pro (with Arg preferred) in P3, and Thr in P4 (Hibino et al., *J Invest. Dermatol.* 90:505–510 (1988); Page et al., *J.B.C.* 266:8142–8148 (1991)).

Guanidinobenzoatases prefer Arg, Arg mimetics or guanidinobenzoyl containing moieties in the P1.

Such inhibitors may be used, for example, to inhibit cancer cell growth.

Thrombin, which hydrolyzes fibrinogen to form fibrin and release fibrinopeptides, prefers Arg in P1 and Gly in P2. Inhibitors may be used, for example, to treat coagulopathies.

For chymase, Tyr and Phe are preferred in P1 although Trp and Leu are accepted. Where the substrate or inhibitor is truncated, there is a strong preference for Pro in P2. In addition, His is preferred in P3, Ile in P4 and Tyr in P5. Inhibitors of chymase may be used, for example, to treat hypertension as well as progressing myocardial deterioration.

Mast cell tryptase, which acts on vasoactive octaicosapeptide, fibrinogen and fibronectin and other substrates, prefers Arg in P1; Gly in P2, although Val, Arg, Leu and Phe are also accepted; and Leu or Arg in P3, while Lys, Ser and Phe are also acceptable. Inhibitors may be used to treat asthma, allergies, arthritis, cutaneous mastocytosis and psoriasis (Tanaka et al., *J.B.C.*, 258:13552–13557 (1983); Caughey, *Am. J. Respir. Crit. Care Med.* 150:S138–S142 (1994)).

Prolyl oligopeptidase prefers Pro in P1 (Yoshimoto et al., *J.B.C.*, 255:4786–4792 (1980); Tsutsumi et. al, *J. Med. Chem.*, 37:3492–3502 (1994); U.S. Pat. No. 5,506,256). Inhibitors may be used, for example, to treat Alzheimer's disease.

Hepatitis C virus NS3 polyprotein endopeptidase is specific for Cys in P1; prefers Cys over Ala in P2; and Val in P3 and P4 (Steinkuehler et al., *J. Virology*, 70:6694–6700 (1996)). Inhibitors may be used to treat hepatitis C infections.

Human cytomegalovirus protease, which is responsible for production of mature virions and processing of viral assembly protein precursors, prefers small residues in P1, such as Ala; Asn, Asp, Gln, Glu or Lys in P2; Val, Ile or Leu in P3; and Val in P4 (Chen et al., *Cell*, 86:835–843 (1996); Tong, et al., *Nature*, 383:272–275 (1996)).

Assemblins (HSVI protease and HSVII protease) or Herpesvirus assemblin prefer Ala in P1; are flexible with respect to P2, although Gln or Lys are preferred; Leu is preferred over Val and Ile in P3; and Tyr in P4. Inhibitors may be used to treat Herpes virus infections.

In the case of u-plasminogen activator, which hydrolyzes plasminogen to form plasmin primarily in migrating cells, Arg is preferred over Lys in P1; Gly in P2; Ser in P3; and Gly may be preferred in P4. Inhibitors may be used to inhibit cancer invasion and metastasis, and to treat stroke (Lindgren, *Stroke*, 27:1066–1071 (1996); Opdenakker et al., *Cytokine*, 4:251–258 (1992)).

For t-plasminogen activator, which hydrolyzes plasminogen to form plasmin primarily in endothelial cells, Arg is preferred in P1, although Lys may be tolerated; Gly is preferred over Ala in P2; while Arg is required in P3 for uPA vs. tPA specificity. Indications include angiogenesis and neovascularization in cancer, and stroke (Lindgren, *Stroke*, 27:1066–1071 (1996); Opdenakker, et al., *Cytokine*, 4:251–258 (1992); Coombs, *J.B.C.*, 271:4461–4467 (1996)).

In addition to altering the binding moiety Z, the substituent on the heterocycle (i.e., $R_1$) can be varied to further increase the specificity of these compounds toward the desired serine protease. Preferred $R_1$ substituents include methyl, dimethylamino; phenyl or benzyl optionally substituted with methyl, halo, methylenedioxy, methoxy, dimethoxy, trimethoxy, trifluoromethyl and dimethylamino. In addition, the heterocycle's heteroatoms can be varied to enhance the activity of the compound. Preferably, the heterocycle is a 1,2,4-oxadiazole, 1,3,4-oxadiazole or a 1,2,4-triazole.

The compounds of the present invention, salts thereof, and their intermediates can be prepared or manufactured as described herein or by various methods known in the chemical art, as well as by extension and modification of methods previously described (see, for example, WO 96/16080).

An alternative method may be used where suitably protected peptides are converted by the action of an activating coupling reagent such as BOP-Cl or HBTU to a Weinreb amide. For a inhibitor comprising a 1,3,4-oxadiazole heterocycle, the Weinreb amide is then reacted with a 5-substituted 2-lithio-1,3,4-oxadiazole at appropriate temperatures ranging from −78° C. to −25° C. in a suitable solvent such as THF or ether to provide the desired keto-oxadiazoles in a single step. Protecting groups, if present, are then removed to provide the enzyme inhibitors in an efficient and convergent manner. A number of efficient methods to synthesize 5-substituted 1,3,4-oxadiazoles are known in the art. Conveniently, these compounds can be synthesized in a single step by refluxing hydrazides of common carboxylic acids with excess ethyl orthoformate at high temperature. The excess orthoformate is hydrolyzed in the workup and the 5-substituted 1,3,4-oxadiazoles are often obtained in essentially pure form without further purification necessary. The method is illustrated in general form in scheme 1 below.

Scheme 1.

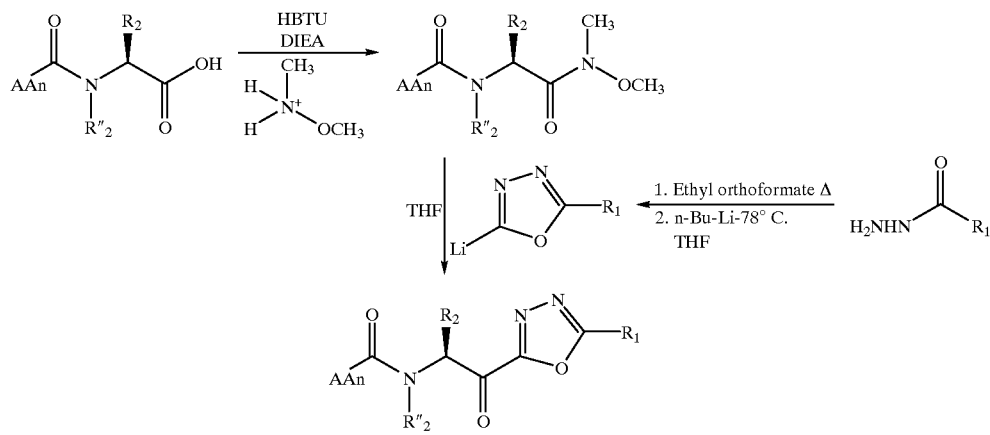

where $AA_n$ means $AA_2 \ldots AA_5$.

The compounds described herein are useful in inhibiting the activity of serine proteases, by contacting the compound with the targeted protease, either in an in vivo or an in vitro environment. As used herein, the term "contacting" means directly or indirectly causing the inhibitor and the protease to come into physical association with each other. Contacting thus includes physical acts such as placing the inhibitor and protease together in a container, or administering the inhibitors to a patient. Thus, for example, administering a compound of the invention to a human patient evidencing a disease or disorder associated with abnormal and/or aberrant activity of such proteases in a method for inhibiting the enzymatic activity of such proteases which are associated with disease or disorder, falls within the scope of the definition of the term "contacting."

Pharmaceutically acceptable salts of serine protease inhibitors described herein may also be used in practicing the methods of the present invention. The term "pharmaceutically acceptable salts" as used here includes organic and inorganic acid addition salts such as chloride, acetate, maleate, fumarate, tartrate and citrate. Examples of pharmaceutically acceptable metal salts are alkali metal salts such as sodium salt or potassium salt, alkaline earth metal salts such as magnesium salt and calcium salt, aluminum salt and zinc salt. Examples of pharmaceutically acceptable ammonium salts are ammonium salt, trishydroxtmethylalinomethane and tetramethylammonium salt. Examples of pharmaceutically acceptable amino acid addition salts are salts with lysine, glycine and phenylalanine.

Although the compounds described herein and/or their salts may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers thereof and, optionally, other therapeutic and or prophylactic ingredients. The carrier(s) must be 'acceptable' in the sense of being compatible with the other ingredients of the composition and not deleterious to the recipient thereof.

Pharmaceutical compositions include those suitable for oral, topical or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservative.

The compounds may also be formulated for parenteral administration (e.g., by injection, for example, bolus injection or continuous infusion) and may be presented in unit dose form in ampules, pre-filled syringes, small bolus infusion containers or in multi-dose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. Nos. 4,931,279, 4668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

The compositions may also be administered via inhalation, using a suitable delivery vehicle.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg/day, e.g., from about 1 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 0.5 to 1000 mg, conveniently 5 to 750 mg, most conveniently, 10 to 500 mg of active ingredient per unit dosage form.

Ideally, the active ingredient should be administered to achieve peak plasma concentrations of the active compound of from about 0.5 to about 75 $\mu$M, more preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 0.5–500 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The inhibitors described herein may be also used for the detection and quantification of the activity of a serine protease in a pure sample, mixture or biological fluid or tissue. The activity can be measured with a protease substrate in the absence and presence of a known concentration of the inhibitor. Specific inhibitors can also be used to confirm that the observed activity is due to a particular protease.

The inhibitors described herein may also be used to identify and purity serine proteases. The inhibitors can be covalently linked to a solid support, such as an affinity column or beads used in batch methods, and used to purify a protease or enrich a mixture containing the protease. The inhibitor may be linked to the solid support or bead either directly, via a linker of variable length such that linkage does not interfere with the binding properties (see, e.g., Thomberry, N., *Methods in Enz.*, 244:615–31 (1994)). Alternatively, the inhibitor may be covalently linked to biotin and arrayed on a solid support via avidin/biotin interaction.

The present invention further provides a method of reducing perioperative blood loss by introducing an inhibitor into a patient directly, or by pretreating, coating or priming medical equipment and devices such as bypass pumps, tubes and catheters, with a suitable liquid composition, or whole blood, comprising one or more inhibitors described herein. Such compositions may also be used to preserve tissues and organs used in transplantation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The following examples are given to illustrate the invention and are not intended to be inclusive in any manner:

EXAMPLES

Example I

Synthesis of N-[N-(4-phenyl-1-ketobutane)-(L)-prolyl]-2-(S)-[(5-(3-phenylpropane)-1,2,4-oxadiazolyl)-ketomethane]-pyrrolidine (CQ-0006)

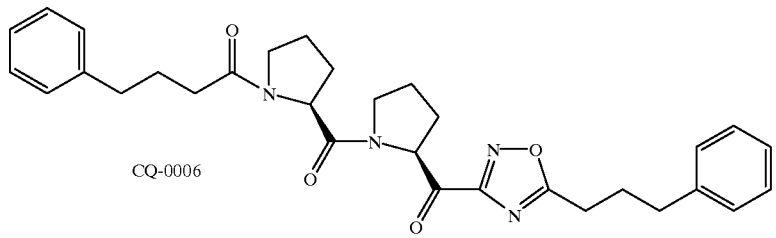

CQ-0006

A. N-Benzyloxycarbonyl-2-(S)-(2-acetoxyethanamide oxime)-pyrrolidine hydrochloride.

To a mixture of N-benzyloxycarbonyl-2-(S)-(2-acetoxyethanenitrile)-pyrrolidine (110.52 g, 0.37 mol) dissolved in 1000 ml of ethanol and 250 ml of water was added hydroxylamine hydrochloride (33.0 g, 0.47 mol), and sodium acetate (45.0 g, 0.55 mol). This mixture was then heated with the temperature maintained between 40–50° C. After 3 hrs. the reaction mixture was concentrated and the residue taken up in ethyl acetate and washed with water. The organic layer was then dried (anhydrous magnesium sulfate), and the solvent evaporated. This material was then converted into its hydrochloride salt (89.23 g, 66%).

B. 4-Phenylbutanoyl chloride.

To a mixture of 4-phenylbutanoic acid (12.0 g, 0.73 mol) in 60 ml of dichloromethane was added oxalyl chloride (12.8 ml, 0.15 mol). This was then stirred at room temperature until gas evolution ceased (2 hrs.). The reaction mixture was then evaporated to yield a yellow oil (13.1 g, 98.1%) which was used without further purification.

IR (neat) 1799.6 cm$^{-1}$ C=O (acid chloride).

C. N-Benzyloxycarbonyl-2-(S)-[N-(4-phenyl-1-keto-butane)-2-acetoxyethanamide oxime]-pyrrolidine.

N-benzyloxycarbonyl-2-(S)-(2-acetoxyethanamide oxime)-pyrrolidine hydrochloride (12.0 g, 0.032 mol) was dissolved in a mixture of toluene (60 ml) and chloroform (35 ml). This mixture was then cooled to 0° C. and triethylamine (6.8 ml, 0.049 mol) was added. After 5 min. 4-phenylbutanoyl chloride (7.0 g, 0.038 mol) in chloroform (15 ml) was added dropwise. The reaction mixture was then allowed to warm to room temperature overnight. After this time the mixture was filtered and the solvent evaporated. This residue was then purified by column chromatography (silica gel; ethyl acetate:hexane, 30:70 to 70:30) to give the product (3.91 g, 25.2%) as a thick oil.

MS 482 (M+1); $^1$HNMR(CDCl$_3$) δ 1.7–2.2 (m, 9H); 2.42 (t2H, J=7.7 Hz); 2.69 (t2H, J=7.7 Hz); 3.3–3.6 (m, 2H); 4.34 (m, 1H); 5.0–5.3 (m, 4H); 5.58 (b, 1H); 7.1–7.4 (m, 10H).

D. N-Benzyloxycarbonyl-2-(S)-[acetoxy-(3-(3-phenylpropane)-1,2,4-oxadiazolyl)-methane]-pyrrolidine.

In toluene (100 ml) was placed N-Benzyloxycarbonyl-2-(S)-[N-(4-phenyl-1-keto-butane)-2-acetoxyethanamide oxime]-pyrrolidine (3.91 g). This mixture was then refluxed for 90 hrs. After this time the reaction was evaporated and the residue purified by column chromatography (silica gel; ethyl acetate:hexane, 0:100 to 50:50) to give the product (2.86 g, 73.7%) as a pale yellow oil.

MS 464 (M+1); $^1$HNMR(CDCl$_3$) δ 1.7–2.3 (m, 9H); 2.39 (t, 2H, J=7.4 Hz); 2.69 (t, 2H, J=7.4 Hz); 3.4–3.7 (m, 2H); 4.0–4.7 (m, 1H); 5.0–5.3 (m, 2H); 5.7–6.4 (m, 1H).

E. N-Benzyloxycarbonyl-2-(S)-[hydroxy-(3-(3-phenylpropane)-1,2,4-oxadiazolyl)-methane]-pyrrolidine.

In methanol (100 ml) was placed N-Benzyloxycarbonyl-2-(S)-[acetoxy-(3-(3-phenylpropane)-1,2,4-oxadiazolyl)-methane]-pyrrolidine (2.86 g, 6.0 mmol). To this was added potassium carbonate (2.0 g, 14.5 mmol) in water (20 ml). This was then stirred at room temperature for 1 hr. At this time the reaction mixture was diluted with ethyl acetate (100 ml) and washed with water (2×100 ml). The organic layer was dried (anhydrous magnesium sulfate) and the solvent evaporated to yield the product (2.36 g, 94.0%) as a pale yellow oil. This was then used without further purification.

F. 2-(S)-[Hydroxy-(3-(3-phenylpropane)-1,2,4-oxadiazol)-methane]-pyrrolidine.

N-Benzyloxycarbonyl-2-(S)-[hydroxy-(3-(3-phenylpropane)-1,2,4-oxadiazolyl)-methane]-pyrrolidine (2.36 g, 5.6 mmol) was dissolved in trifluoroacetic acid (50 ml). This was then cooled to 0° C. and thioanisole (1.0 ml, 8.5 mmol) was added and the reaction allowed to warm to room temperature overnight. After this time the reaction mixture was evaporated and the residue taken up into ether. The ether was extracted with 2N hydrochloric acid and the aqueous layer was washed with ether. The aqueous layer was then neutralized with sodium bicarbonate and then extracted with ether. The organic layer was then dried (anhydrous magnesium sulfate) and evaporated to yield the product (0.46 g. 29.3%) as a yellow oil. This was then used without further purification.

MS 288 (M+1); $^1$H NMR(CDCl$_3$) δ 1.5–2.2 (m, 9H); 2.6–2.7 (m, 2H); 2.8–2.9 (m)2H); 3.4–3.6 (m, 1H); 4.5–4.7 (m, 1H); [4.77 (d, J=9.99), 5.03 (d, J=1.8), 1H]; 5.88 (b, 1H); 7.1–7.4 (m, 5H).

G. N-(4-phenyl-ketobutane)-(L)-proline t-butyl ester.

To a solution of (L)-proline t-butyl ester hydrochloride (5.0 g, 0.024 mol) in toluene (50 ml) and chloroform (30 ml), at 0° C., was added triethylamine (5.0 ml, 0.036 mol). After 5 min., 4-phenylbutanoyl chloride (5.0 g, 0.027 mol) was added and the reaction allowed to warm to room temperature overnight. After this time the reaction mixture was filtered and the solvent evaporated. The residue was then purified by column chromatography (silica gel; ethyl acetate:hexane, 0:100 to 50:50) to yield the product (5.0 g, 65.4%) as a pale yellow oil.

MS 318 (M+1); $^1$H NMR(CDCl$_3$) δ [1.42 (s), 1.46 (s), 9H]; 1.8–2.4 (m, 8H); 2.68 (t, 2H, J=7.4); 3.3–3.7 (m, 2H); [4.17 (dd, J=2.8, J=8.5),4.39 (dd, J=3.6, J=8.5), 1H]; 7.1–7.4 (m, 5H).

H. N-(4-phenyl-ketobutane)-(L)-proline.

To a solution of N-(4-phenyl-ketobutane)-(L)-proline t-butyl ester (5.0 g) in dichloromethane (50 ml), cooled to 0° C., was added trifluoroacetic acid (20 ml). After 3 hrs. the reaction mixture was concentrated and then taken up in ethyl acetate. This was then extracted with 2N sodium hydroxide solution. This aqueous solution was then washed with ethyl acetate before it was neutralized with 4N hydrochloric acid. Then the aqueous layer was extracted with ethyl acetate and the organic layer dried (anhydrous magnesium sulfate) and the solvent evaporated. This yielded the product (4.1 g, >95%) as a thick oil.

MS 262 (M+1); $^1$H NMR(CDCl$_3$) δ 1.8–2.3 (m, 4H); 2.38 (t, 2H, J=7.1 Hz); 2.69 (t, 2H, J=7.4 Hz); 3.3–3.6 (m, 2H); 4.57 (q, 1H, J=4.0); 7.1–7.4 (m, 5H); 12.08 (s, 1H).

I. N-[N-(4-Phenyl-1-ketobutane)-(L)-prolyl]-2-(S)-[hydroxy-(3-(3-phenylpropane)-1,2,4-oxadiazolyl)-methane]-pyrrolidine.

In dry dimethylformamide (20 ml) at 0° C., was placed N-(4-phenyl-ketobutane)-(L)-proline (0.46 g, 1.76 mmol) along with HOBT (0.30 g, 2.29 mmol) and EDCI (0.35, 1.94 mmol). This was then kept at 0° C. for 30 min. After this time 2-(S)-[Hydroxy-(3-(3-phenylpropane)-1,2,4-oxadiazolyl)-methane]-pyrrolidine (0.48 g, 1.94 mmol) along with N-methyl morpholine (0.28 ml, 2.64 mmol) were added dropwise. This mixture was then allowed to stir at 0° C. overnight. At which time the mixture was diluted with ethyl acetate and washed with saturated sodium bicarbonate, potassium hydrogen sulfate, and water. The organic layer was then dried (anhydrous magnesium sulfate) and the solvent evaporated. The remaining residue was purified by column chromatography (silica gel; ethyl acetate:hexane, 50:50) followed by RP-HPLC (acetonitrile:water, 40:60) to give the product (0.25 g, 26.8%) as a clear oil after lyophilization.

MS 531 (M+1); $^1$H NMR(CDCl$_3$) δ 1.8–2.4 (m, 16H); 2.6–2.8 (m, 4H); 2.8–3.0 (m, 2H); 3.35–3.50 (m, 1H);

3.55–3.70 (m, 1H); 3.85–4.00 (m, 1H); 4.6–4.8 (m, 2H); 4.95 (d, 1H, J=1.9 Hz); 7.1–7.4 (m, 10H).

J. N-[N-(4-phenyl-1-ketobutane)-(L)-prolyl]-2-(S)-[(3-(3-phenylpropane)-1,2,4-oxadiazolyl)-ketomethane]-pyrrolidine.

In dry toluene (10 ml) was placed N-chlorosuccinimide (0.25 g, 1.89 mmol) and this was cooled to 0° C. Then dimethylsulfide (0.20 ml, 2.69 mmol) was added and allowed to stir for 30 min. at 0° C. After this time the mixture was cooled to −25° C. and N-[N-(4-Phenyl-1-ketobutane)-(L)-prolyl]-2-(S)-[hydroxy-(3-(3-phenylpropane)-1,2,4-oxadiazolyl)-methane]-pyrrolidine (0.25 g, 0.47 mmol) in dry toluene (20 ml) was added dropwise. After 1 hr. TEA (triethylamine)(0.19 gm, 1.89 mmol) was added and the mixture was allowed to warm to room temperature. The resulting mixture was diluted with ethyl acetate and washed with saturated sodium bicarbonate and brine. The organic layer was then dried (anhydrous magnesium sulfate) and the solvent evaporated. The residue was then purified by RP-HPLC (acetonitrile:water, 15:85 to 100:0) to yield the product (0.16 g, 64%) as a clear oil after lyophilization.

MS 529 (M+1); $^1$H NMR(CDCl$_3$) δ 1.8–2.4 (m, 14H); 2.65 (t, 2H, J=7.7 Hz); 2.72 (t, 2H, J=7.4 Hz); 2.93 (t, 2H, J=7.4 Hz); 3.32–3.46 (m, 1H); 3.5–3.6 (m, 1H); 3.66–3.76 (m, 1H); 3.9–4.02 (m, 1H); 4.66–4.74 (m 1H); 5.46 (q, 1H, J=3.1 Hz, J=5.5 Hz); 7.1–7.4 (m, 10H). $^{13}$CNMR(CDCl$_3$) δ 24.62, 25.33, 25.83, 25.96, 27.84, 28.40, 28.43, 33.57, 34.90, 35.25, 47.05, 47.12, 47.24, 57.45, 62.92, 75.40, 75.83, 76.26, 125.83, 126.32, 128.31, 128,50, 128.54, 128.58, 140.40, 141.80, 164.41, 170.70, 171.65, 181.10, 189.62. $C_{31}H_{36}O_4N_4$.

|  | % C | % H | % N |
|---|---|---|---|
| Theory | 70.42 | 6.87 | 10.60 |
| Found | 69.97 | 6.73 | 10.12 |

Example II

Synthesis of Acetyl-L-leucyl-N-[1-[2-[(5-phenyl)-1,3,4-oxadiazolyl]carbonyl]-4-(guanidino)-butyl]-L-leucyl]amide) (CQ-0002)

2-Phenyl-1,3,4-oxadiazole intermediate

Benzoyl hydrazide (200 mg) freshly crystallized from chloroform was suspended in 5 mL of triethyl orthoformate and heated at reflux under nitrogen in a 160° C. oil bath for 3 hours. The mixture was cooled to room temperature, chilled in ice, and treated with 50 mL water and 10 mL 10% KHSO$_4$ solution. The mixture was stirred approximately 2 minutes then 50 mL of EtOAc was added and stirring continued for 10 minutes, The organic layer was separated and the aqueous layer was extracted three times with ethyl acetate. All ethyl acetate layers were combined and were washed with 10% sodium bicarbonate solution and saturated sodium chloride solution. Drying over sodium sulfate, rotary evaporation and further drying under high vacuum provided 204 mg of an analytically pure oil which crystallizes upon standing. Commercially available benzoylhydrazide (Aldrich) in this reaction may be used, but the resulting product often contains a minor impurity which can be removed following the cyclization, by flash chromatography on silica gel eluting with 0–10% acetone in hexane.

$^1$H-NMR-CDCl$_3$ 7.49–7.62 (m, 3H), 8.12 (d, J-6, 2H), 8.49 (s, 1H).

A. Acetyl-L-leucyl-L-leucyl-arginine(Mtr) (N-methyl)-(N-Methoxy)-amide: Acetyl-Leu-Leu-OH (133 mg) and arginine (Mtr)-N-methyl-N-methoxy amide (200 mg) were dissolved in 10 mL of DMF and were treated with 243 uL of DIEA and 212 mg of HBTU. The reaction stirred at room temperature for 15 hours and was worked up according to method A. Drying over Na$_2$SO$_4$, rotary evaporation of the solvent and flash chromatography on silica gel (50% acetone in hexane) provided 270 mg of the title compound as a foam.

B. Acetyl-L-leucyl-N-[1-[2[(5-phenyl)-1,3,4-oxadiazolyl]carbonyl]-4-](4-methoxy-2,3,6-trimethyl-benzenesulphonyl)-guanidino[-butyl]-L-leucyl amide: 2-phenyl-1,3,4-oxadiazole (194 mg) in 2 mL of dry THF was chilled to −78° C. n-Butyllithium (1.46 mmole) was added as a 2.5 M solution in hexanes. The reaction stirred 20 minutes at −78° C. and was then placed in a 0° C. cooling bath. Acetyl-Leu-Leu-Arg-(Mtr)-N—(CH$_3$)—OCH$_3$ was then added in 2 mL of dry THF. The reaction was placed in a room temperature water bath and stirred 1 hour, then the solution was chilled to 0° C., and 20 mL of saturated ammonium chloride solution was added under nitrogen with rapid stirring. After the several minutes of vigourous stirring the solution was extracted with EtOAc. The ethyl acetate solution was washed with saturated sodium chloride solution, dried over sodium sulfate and concentrated to a pale brown oil by rotary evaporation.

C. Acetyl-L-leucyl-N-[1-[2-[(5-phenyl)-1,3,4-oxadiazolyl]carbonyl]-4-(guanidino)-butyl]-L-leucyl amide: One half of the crude product from step B was dissolved in a pre-formed solution of 2 mL of TFA and 100 uL thioanisole. The reaction stirred under nitrogen for 4 hours. The solvent was removed in vacuo, and the product was precipitated with dry ether. The precipitate was taken up in methanol and concentrated in vacuo, the residue was triturated with dry ether, and dried in vacuo to provide 22 mg of the title compound as a colorless powder. Samples for biological testing were obtained by reverse phase C18 chromatography (5–80% CH$_3$CN, 0.1% TFA, over 40 minutes). MS m/z (M+H) 571 (CQ-0002).

Example III

Measurement of Inhibitory Activity Against Trypsin

For K$_i$ measurement, bovine pancreatic trypsin (Sigma) was prepared at a concentration of 0.2 mg/mL in 0.05 M acetate buffer (pH5.1) containing 0.1M NaCl, 10 mM CaCl$_2$, 0.005% Triton X-100 (v/v). The working stock of CQ-0002 was prepared in 0.1M HEPES buffer at pH 7.5, containing 0.1M NaCl, 10 mM CaCl$_2$, 0.005% Triton X-100 (v/v), 10% DMSO (v/v). The reaction was started by mixing enzyme (2 μg/mL final concentration), inhibitor and substrate (D/L BAPNA, 2 mM final concentration) simultaneously in the assay buffer (0.1M HEPES, 0.1M NaCl, 10 mM CaCl$_2$, 0.005% Triton X-100 (v/v), 5% DMSO (v/v), pH7.5). Release of nitroaniline was monitored spectrophotometrically at 410 nm over a 10 min time span at room temperature. Steady-state velocities were measured at different inhibitor concentrations and the IC$_{50}$ value was calculated using ENZFIT (Elsevier). The K$_i$ constant was calculated as: K$_i$=IC$_{50}$ [I+(S/K$_m$)]. Results are presented in Table 1.

Example IV

Measurement of Inhibitory Activity Against Proteinase 3 (PR-3)

The assays are performed essentially as described in the literature (Hoidal, et al., *Meth. in Enzymol.*, 244:61–67 (1994); Fruh, et al., *Biol. Chem.*, 377:579–586 (1996)). However, human neutrophil proteinase 3 (Athens Research and Technology, Inc.) was unstable during the assay. To prevent inactivation due to adsorption or aggregation of the enzyme, proteinase 3 was diluted 1:40 using 0.05 M acetate buffer, containing 0.1 M NaCl and 0.005% Triton-X 100, pH 5.1. Proteinase 3 was stable due to the presence of Triton X-100 during 4–6 hours on ice without any loss of activity. 50 mM Boc-Ala-OPhNO$_2$ in DMSO was used as a substrate, final concentration was 0.625 mM. Residual activity of the enzyme was determined after preincubation of the enzyme (6 μl) with different concentrations of inhibitors at 25° C. in 0.1 M HEPES buffer, containing 0.1 M NaCl, 10 mM CaCl$_2$, 0.0005% Triton X-100 and 5% DMSO, pH 7.5. The release of nitrophenol was monitored at 410 nm, Results are presented in Table 1.

Example V

Measurement of Inhibitory Activity Against Human Tryptase

Each compound was diluted in 0.12M NaCl and added to 1 mL of 0.2 mM tosyl-Gly-Pro-Lys-p-nitroanilide in 40 mM HEPES, pH 7.4, at room temperature. Enzymatic reactions were initiated by addition of 30 ng of purified human lung-derived tryptase that had been stabilized with 150 ng of Dextran sulfate. Initial velocities were monitored spectrophotometrically at 410 nm over a 1.5 min time span. Percent inhibition was calculated as: $[(v_0-v_j)/v_0] \times 100$.

Example VI

Measurement of Inhibitory Activity Against Prolyl Oligopeptidase

The enzyme prolyl oligopeptidase (flavobacterium) and the substrate Z-Gly-Pro-NHMec 9-NHMec: 7-(4-methylcoumarylamide) were obtained from Sigma (St. Louis, Mo.). The enzyme assay was performed as described elsewhere (Tadashi Yoshimoto et al., *J. Biol. Chem.*, 255, 4786–4792, 1980), except that a Quanta Master QM1 (Photon Technologies Tnternational, South Brunswick, N.J.) was used and S<<K$_m$. The inhibitor was preincubated for 20 min at room temperature with the enzyme before starting the reaction by adding substrate. Four inhibitor concentrations were used to estimate the IC$_{50}$ value which approximates the K$_i$ constant directly (Cheng, et al., *Biochemical Pharmacology*, 22:3099–3108).

Example VII

Measurement of Inhibitory Activity Against Bovine α-Chymotrypsin (α-chym), Porcine Pancreatic Elastase (PPE) and Human Cathepsin-G (Cat-G)

Buffers were prepared as follows: 0.1 M HEPES, 0.1M NaCl, 10 nM CaCl$_2$, 0.005% Triton X-100, pH7.5 (assay buffer); 0.05M NaCH$_3$CO$_2$, 0.1M NaCl, 10 mM CaCl$_2$, pH 5.1 (enzyme dilution buffer).

The following substrates were used: N-succinyl-Ala-Ala-Pro-Leu-pNA (α-chym, PPE) was prepared as a 200 mM stock in DMSO. N-succinyl-Ala-Ala-Pro-Phe-pNA (Cat-G) was prepared as a 100 mM stock in DMSO. The final substrate concentrations for the assays were 0.5 mM, 1.0 mM and 2.0 mM for α-chym, Cat-G and PPE, respectively.

The enzyme α-chym was in a 2.0 mg/ml stock solution. An aliquot was diluted to 0.025 mg/ml in the enzyme dilution buffer. PPE was a 2.0 mg/ml solution. The material was diluted to 0.05 mg/ml in dilution buffer. Cat-G (1 mg) was prepared at a concentration of 2 mg/ml in dilution buffer as a stock. Aliquots of this were further diluted to 0.2 mg/ml.

The following reagents were applied to 1-ml cuvettes (Dynalab): 0.945 ml assay buffer; (40-x) μl DMSO (final concentration of DMSO was 5%);xμl diluted inhibitor (from 10 mM stocks); and 10 μl substrate. The reaction was commenced with the addition of enzyme (5 μl). The formation of product p-nitroaniline was monitored at 410 nm in a spectrophotometer over 15–30 min. Steady-state velocities were determined and processed using a software program (ENZFIT, Elsevier), generating the IC$_{50}$ values. From these data, the K$_i$ values were determined using the equation: K$_i$=I$_{50}$/[1+([S]/K$_m$)]. Results are presented in Table 1.

TABLE 1

| Compound | trypsin[a] | tryptase[b] | prolyloligo peptidase | proteinase 3[a] | chymo-trypsin[a] | PPE[a] | Cat-G[a] | HLE[a] |
|---|---|---|---|---|---|---|---|---|
| leupeptin | | 175 | | | | | | |
| CQ-0002 | 0.62 | 25 | | | | | | |
| CQ-0006 | | | ≦1 | | | | | |
| CE-2036 | | | | | | 28.0 | | 2 |
| CE-2048 | | | | 24.0 | | 5.5 | | <1 |
| CE-2056 | | | | | | 26.0 | | <1 |
| CE-2061 | | | | | 0.17 μM | | 1.2 μM | |
| CE-2064 | | | | | | 21.6 | | <1 |
| CE-2072- | | | | 5.0 | 32.0 | .6 | | <1 |
| CE-2077- | | | | 62.0 | | 4.7 | | <1 |
| CE-2081 | | | | | | 16.0 | | |
| CE-2083 | | | | | | 41.0 | | 73 |
| CE-2093 | | | | | | 8.0 | | <1 |
| CE-2099- | | | | 28.0 | | | | 1.9 |
| CE-2104- | | | | 35.6 | | | | <1 |
| CE-2126- | | | | | | 72.0 | | 5 |

-continued
| Compound | trypsin[a] | tryptase[b] | prolyloligo peptidase | proteinase 3[a] | chymo-trypsin[a] | PPE[a] | Cat-G[a] | HLE[a] |
|---|---|---|---|---|---|---|---|---|
| CE-2145- | | | | 9.6 | | 1.3 | | <1 |
| CE-2149- | | | | 6.5 | | | | <1 |
| CE-2152 | | | | 44.7 | | | | <1 |
| CE-2161 | | | | 22.0 | | 1.2 | | <1 |
| CE-2163 | | | | 57.0 | | | | <1 |
| CL-2168 | | | | 63.0 | | | | <1 |
| CE-2171 | | | | 63.0 | | | | <1 |
| CE-2183 | | | | 10.5 | | | | <1 |
| CE-2185 | | | | 80.0 | | | | <1 |
| CE-2186 | | | | 14.3 | | | | <1 |
| CE-2195 | | | | 19.4 | | | | 10.6 |
[a]= $K_i$;
[b]= $IC_{50}$;
(units nM unless otherwise indicated);
HLE = human leukocyte elastase
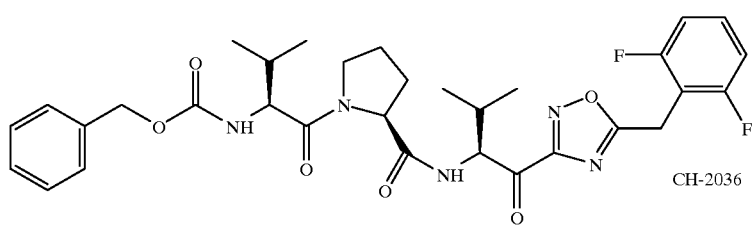
CH-2036
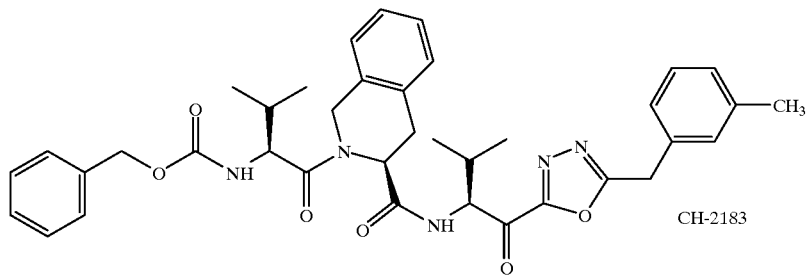
CH-2183
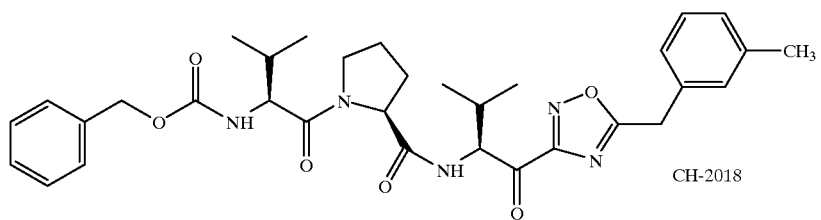
CH-2018
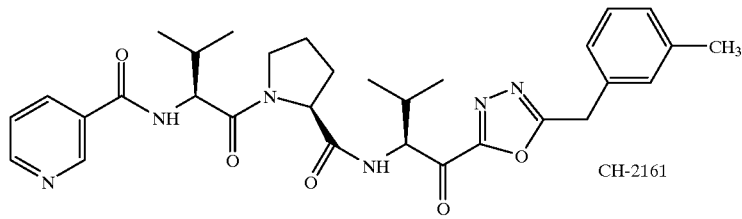
CH-2161

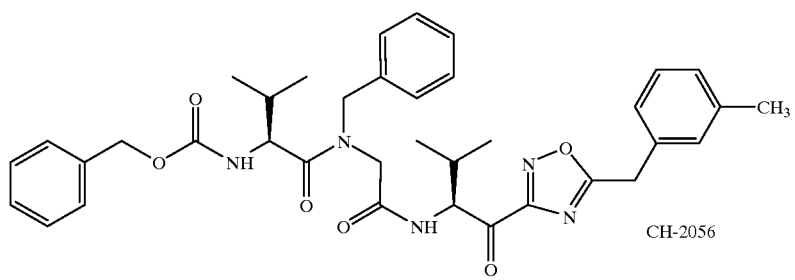
CH-2056
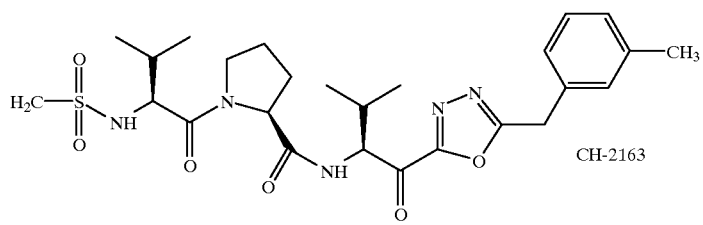
CH-2163
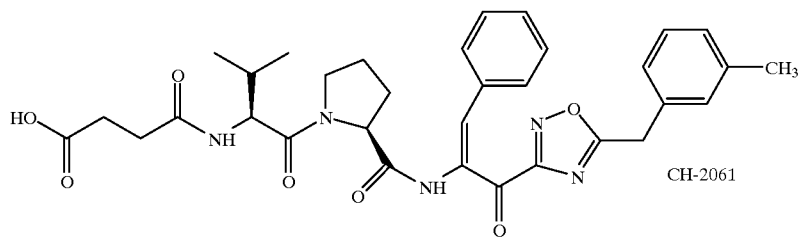
CH-2061
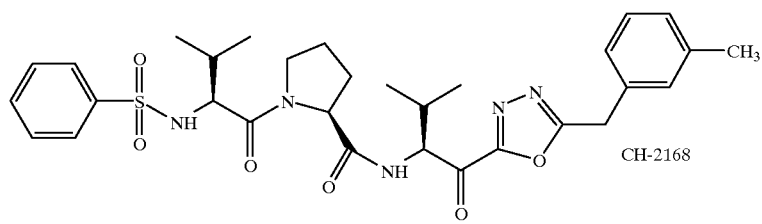
CH-2168
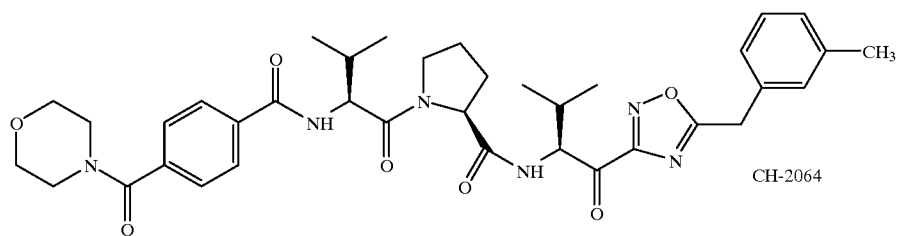
CH-2064
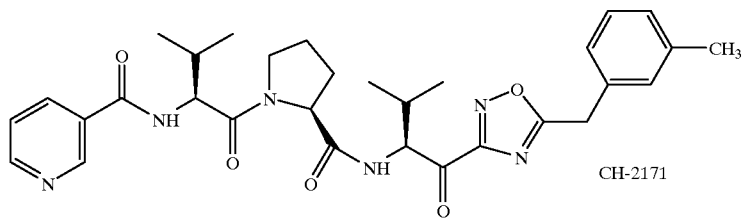
CH-2171
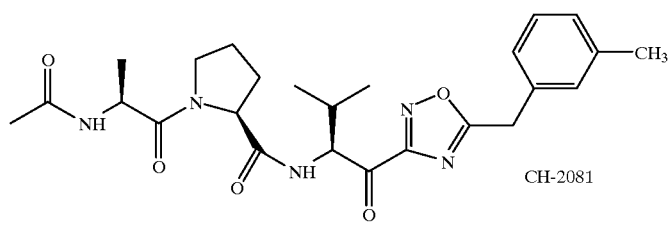
CH-2081

-continued
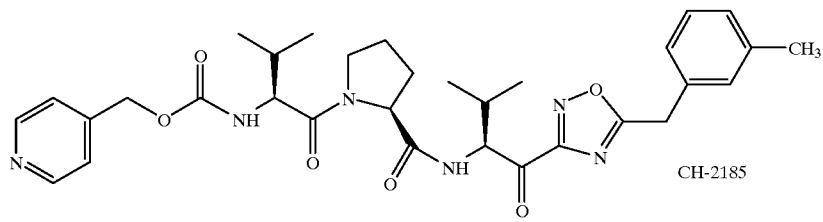
CH-2185
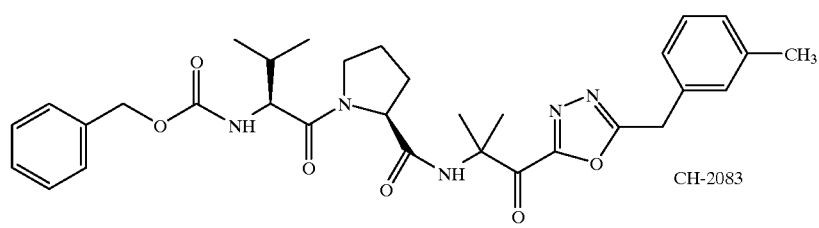
CH-2083
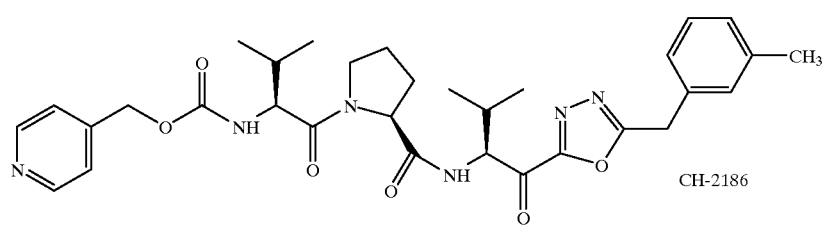
CH-2186
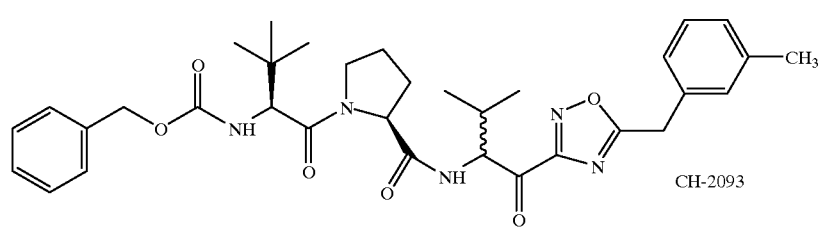
CH-2093
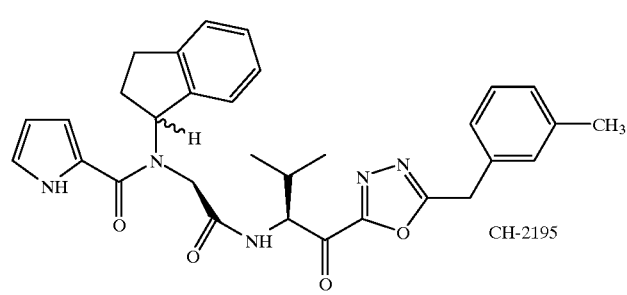
CH-2195
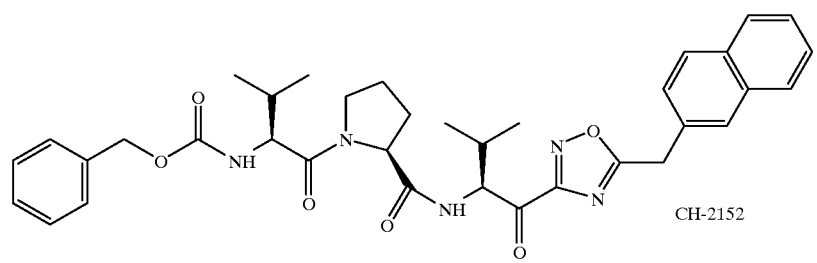
CH-2152

We claim:

1. A method of inhibiting the enzymatic activity of a serine protease selected from the group consisting of thrombin, plasmin, plasma kallikrein, tissue kallikrein, guanidinobenzoatase, chymase, mast cell tryptase, prolyl oligopeptidase hepatitis C virus NS3 polyprotein endopeptidase, human cytomegalovirus protease, assemblin, $\mu$-plasminogen activator, tissue plasminogen activator, and Schistosoma serine protease; wherein the method comprises contacting such protease with an inhibitory amount of a compound of formula (I):

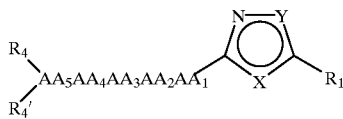

(I)

wherein $AA_1$, $AA_2$, $AA_3$, $AA_4$ and $AA_5$ are independently an amino acid residue or amino acid residue mimetic, or a direct bond;

$R_4$ and $R_4'$ are independently —C(O)R$_5$, —C(O)NHR$_5$, —S(O)$_2$R$_5$, —C(O)OR$_5$, —C(O)-(C$_5$–C$_6$)aryl-C(O)—R$_5$, —CH$_2$R$_5$ or R$_5$, where R$_5$ is H, alkyl, alkenyl or alkynyl optionally substituted with halo, cyano, nitro, hydroxy, alkoxy, haloalkyl, amino, aminoalkyl, dialkylamino, haloalkoxy, carboxyl, carboalkoxy or alkylcarboxamide; cycloalkyl, alkylcycloalkyl, (C$_5$–C$_{12}$)aryl or (C$_5$–C$_{12}$)arylalkyl optionally comprising 1–4 heteroatoms selected from N, O and S, and optionally substituted with halo, cyano, nitro, hydroxy, alkoxy, haloalkyl, amino, aminoalkyl, dialkylamino, haloalkoxy, carboxyl, carboalkoxy, alkylcarboxamide, alkyl, alkenyl, alkynyl or (C$_5$–C$_{12}$)aryl; or are absent; or together R$_4$ and R$_4'$ form a ring comprising 5–7 atoms selected from C, N, S and O;

R$_1$ is alkyl or alkenyl optionally substituted with 1–3 halo or hydroxy; alkylamino, dialkylamino, alkyldialkylamino; or cycloalkyl, alkylcycloalkyl, alkenylcycloalkyl, (C$_5$–C$_{12}$)aryl, (C$_5$–C$_{12}$)arylalkyl or (C$_5$–C$_{12}$)arylalkenyl optionally comprising 1–4 heteroatoms selected from N, O and S, and optionally substituted with halo, cyano, nitro, hydroxy, alkylenedioxy, haloalkyl, amino, aminoalkyl, dialkylamino, alkyl, alkenyl, alkynyl, alkoxy, haloalkoxy, carboxyl, carboalkoxy, alkylcarboxamide, (C$_5$–C$_6$)aryl, —O—(C$_5$–C$_6$)aryl, arylcarboxamide, alkylthio or haloalkylthio; and Y and X are independently O, S or N, said N being optionally substituted with (a) alkyl or alkenyl, which alkyl or alkenyl is optionally substituted with 1–3 halo atoms; or (b) (C$_5$–C$_6$)aryl, arylalkyl or arylalkenyl optionally comprising 1–3 heteroatoms selected from N, O and S, and optionally substituted w halo, cyano, nitro, hydroxy, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio;

wherein at least one of Y or X is N; or a pharmaceutically acceptable salt thereof;

provided that:

(a) if the serine protease is thrombin, then AA$_2$ is Gly;
(b) if the serine protease is plasmin, then AA$_1$ is Lys, AA$_2$ is Phe, AA$_3$ is Pro, and AA$_4$ and AA$_5$ together form a direct bond from AA$_3$ to $_4$ and R$_4'$ is absent;
(c) if the serine protease is plasma kallikrein, then (i) AA$_1$ is Arg or Arg mimetic or substituted or unsubstituted Lys; (ii) AA$_2$ is Phe, Met, or Leu; (iii) AA$_3$ is Pro; and AA$_4$ and AA$_5$ together form a direct bond from AA$_3$ to R$_4$and R'$_4$ is absent.

2. A method of claim 1 wherein AA$_1$, AA$_2$, AA$_3$, AA$_4$, and AA$_5$ are an amino acid residue or an amino acid residue mimetic.

3. A method of claim 1 wherein AA$_5$ is a bond from AA$_4$ to R$_4$ or a bond from AA$_4$ to R'$_4$ or separate bonds from AA$_4$ to R$_4$ and from AA$_4$ to R'$_4$.

4. A method of claim 1 wherein AA$_5$ and AA$_4$ together form a bond from AA$_3$ to R$_4$ or a bond from AA$_3$ to R'$_4$, or separate bonds from AA$_3$ to R$_4$ and from AA$_3$ to R'$_4$.

5. A method of claim 1 wherein AA$_5$, AA$_4$, and AA$_3$ together form a bond from AA$_2$ to R$_4$, or a bond from AA$_2$ to R'$_4$, or separate bonds from AA$_2$ to R$_4$ and from AA$_2$ to R'$_4$.

6. A method of claim 1 wherein the amino acids are selected from arginine or an arginine mimetic; proline; aspartic and glutamic acid and the aryl and alkyl esters thereof; alanine and glycine optionally substituted at the α-carbon or α-nitrogen with alkyl, cycloalkyl or aryl; leucine, isoleucine, cysteine optionally substituted at the sulfur atom with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homophenylalanine, dehydro-phenylalanine, indoline-2 carboxylic acid; tetrahydroisoquinoline-2-carboxylic acid optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; tyrosine, serine or threonine optionally substituted with alkyl or aryl; tryptophan, histidine, methionine, valine, norvaline, norleucine, octahydroindole-2-carboxylic acid; asparagine, glutamine, ornithine and lysine optionally substituted at the sidechain nitrogen atom with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S.

7. A method of claim 1 wherein $AA_1$ is an amino acid residue or amino acid residue mimetic, or of the formula (IIIa):

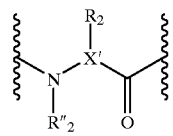

wherein X' is $CR_2'$; and $R_2$, $R_2'$ and $R_2''$ are independently H; alkyl or alkenyl optionally substituted with 1–3 halo, hydroxy, thio, alkylthio, amino, alkylamino, dialkylamino, alkylguanidinyl, dialkylguanidinyl, guanidinyl or amidylguanidine; —RCOR', —RCOOR', —RNR'R"R° or —RC(O)NR'R" where R is alkyl or alkenyl, and R', R" and R° are independently H, alkyl, alkenyl, cycloalkyl or $(C_5-C_6)$aryl; or cycloalkyl, alkylcycloalkyl, alkenylcycloalkyl, alkyl-oxyaryl, alkyl-thioaryl, alkyl-aminoaryl, $(C_5-C_{12})$aryl, $(C_5-C_{12})$arylalkyl or $(C_5-C_{12})$arylalkenyl optionally comprising 1–4 heteroatoms select from N, O and S, and optionally substituted with hydroxy, halo, cyano, keto, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, $(C_5-C_6)$aryl, —O-$(C_5-C_6)$aryl, arylcarboxamide, alkylthio or haloalkylthio; or $R_2$, and $R_2'$ together with X' form a ring comprising 4–7 atoms selected from C, N, S and O, said ring optionally substituted with hydroxy, halo, cyano, nitro, haloalkyl, amino, aminoalkyl, dialkylamino, amidine, alkylamidine, dialkyl amidine, alkyl, alkenyl, alkynyl, alkoxy, haloalkoxy, carboxyl, carboalkoxy, alkylcarboxamide, $(C_5-C_6)$aryl, —O-$(C_5-C_6)$aryl, arylcarboxamide, alkylthio or haloalkylthio.

8. A method of claim 7 wherein $AA_2$ is an amino acid residue, or of the formula (IIIb):

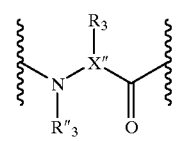

or selected from a mimetic of formulas IV to XXIV:

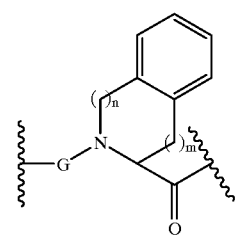

(IV)

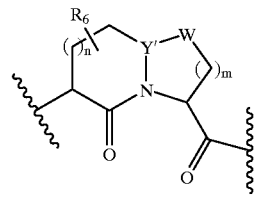

(V)

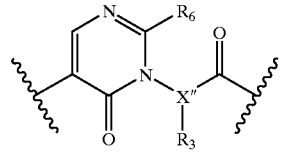

(VI)

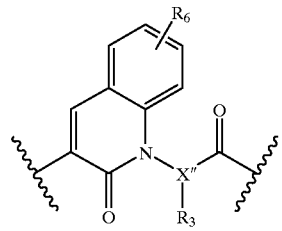

(VII)

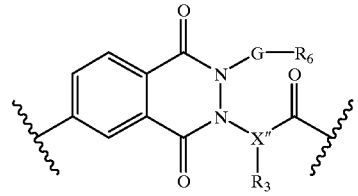

(VIII)

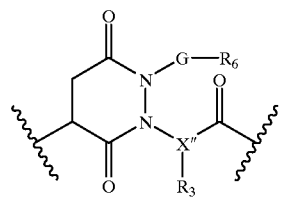

(IX)

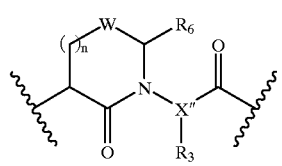 (X)
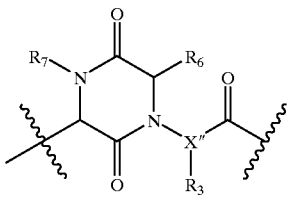 (XI)
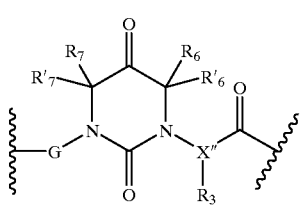 (XII)
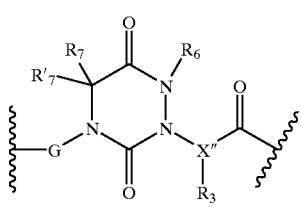 (XIII)
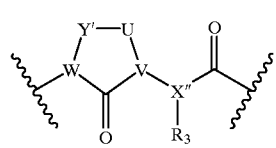 (XIV)
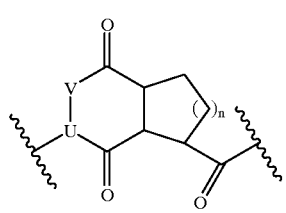 (XV)
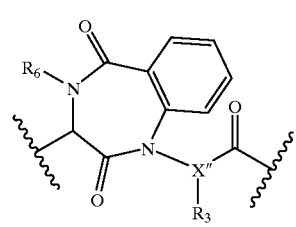 (XVI)
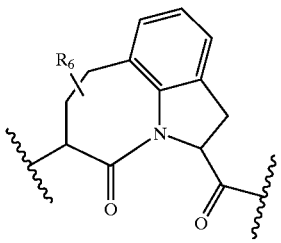 (XVII)
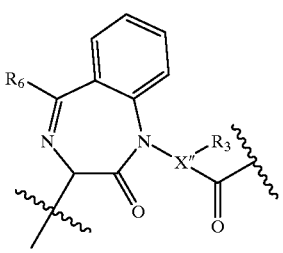 (XVIII)
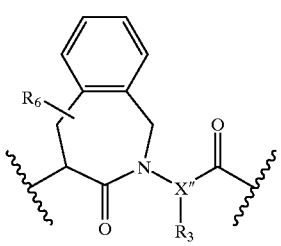 (XIX)
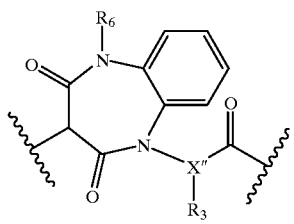 (XX)
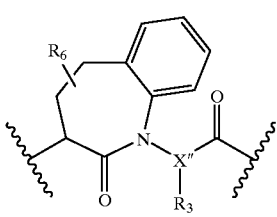 (XXI)
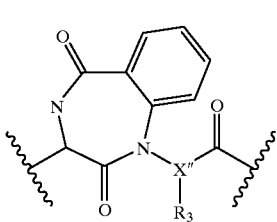 (XXII)

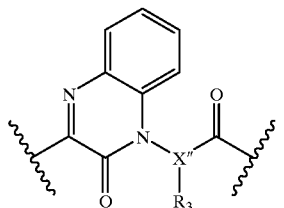

(XXIII)

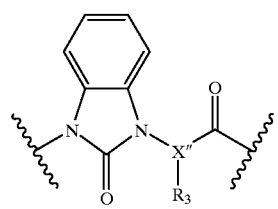

(XXIV)

wherein X" is CR'₃;

R₃, R'₃ and R"₃ are independently H; alkyl or alkenyl optionally substituted with 1–3 halo, hydroxy, thio, alkylthio, amino, alkylamino, dialkylamino, alkylguanidinyl, dialkylguanidinyl, guanidinyl or amidylguanidine; —RCOR', —RCOOR', —RNR'R"R° or —RC(O)NR'R" where R is alkyl or alkenyl, and R', R" and R° are independently H, alkyl, alkenyl, cycloalkyl or (C₅–C₆)aryl; or cycloalkyl, alkylcycloalkyl, alkenylcycloalkyl, alkyl-oxyaryl, alkyl-thioraryl, alkyl-aminoaryl, (C₅–C₁₂)aryl, (C₅–C₁₂)arylalkyl or (C₅–C₁₂)arylalkenyl optionally comprising 1–4 heteroatom selected from N, O and S, and optionally substituted with hydroxy, halo, cyano, keto, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, (C₅–C₆)aryl, —O-(C₅–C₆)aryl, arylcarboxamide, alkylthio or haloalkylthio;

m is 0, 1 or 2;

n is 0, 1 or 2;

G is —C(O)—, —NHC(O)—, —S(O)₂—, —OC(O)—, —CH₂— or a direct bond;

R₆, R₇, R'₆, R'₇ are independently H, alkyl, alkenyl, halo, alkoxy, carboxyl, carboalkoxy, amino, aminoalkyl, dialkylamino; cycloalkyl, (C₅–C₆)aryl or (C₅–C₆) arylalkyl optionally comprising 1–3 heteroatoms selected from N, O and S, and optionally substituted with alkyl, alkenyl, alkynyl, halo, cyano, nitro, hydroxy, haloalkyl, amino, alkylamino, dialkylamino, alkoxy, haloalkoxy, carboxyl, carboalkoxy, alkylcarboxamide, alkylthio, guanidine, alkylguanidine, dialkylguanidine, amidine, alkylamidine or dialkylamidine; and U, V, W and Y' are independently or together N, C, C(O), N(R₉) where R₉ is H, alkyl, halo, alkoxy, carboalkoxy, cycloalkoxy, carboxyl, alkylthio, amino, alkylamino, dialkylamino, or aryl, fused aryl or cycloalkyl optionally comprising 1 or more heteroatoms selected from O, S and N, and optionally substituted with halo or alkyl; N(R₁₀) where R₁₀ is H, alkyl, alkenyl or cycloalkyl, aryl, arylalkyl or fused aryl-cycloalkyl optionally comprising 1–4 heteroatoms selected from N, O and S, and optionally substituted with alkyl, alkenyl, alkynyl, halo, cyano, nitro, haloalkyl, hydroxy, amino, alkylamino, dialkylamino, alkoxy, haloalkoxy, carboxyl, carboalkoxy, alkylcarboxamide, alkylthio, guanidine, alkylguanidine, dialkylguanidine, amidine, alkylamidine or dialkylamidine; or C(R₁₁)(R₁₂) where R₁₁ and R₁₂ are independently or together H, alkyl, alkylthio, alkylthioalkyl or cycloalkyl, alkylcycloalkyl, phenyl or phenyl alkyl optionally substituted with guanidine, carboalkoxy, hydroxy, haloalkyl, alkylthio, alkylguanidine, dialkylguanidine, amidine, alkylamidine or dialkylamidine.

9. A method of claim 8 wherein AA₃, AA₄, and AA₅ are independently a direct bond or an amino acid selected from arginine or an arginine mimetic; proline; aspartic and glutamic acid and the aryl and alkyl esters thereof; alanine or glycine optionally substituted at the α-carbon or α-nitrogen with alkyl, cycloalkyl or aryl; leucine, isoleucine; cysteine optionally substituted at the sulfur atom with alkyl, alkenyl or phenyl optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; phenylalanine, homo-phenylalanine, dehydrophenylalanine, indoline-2 carboxylic acid; tetrahydroisoquinoline-2-carboxylic acid optionally substituted with halo, cyano, nitro, haloalkyl, amino, aminoalkyl, dialkylamino, alkyl, alkoxy, haloalkoxy, carboxyl, carboalkoxy, alkylcarboxamide, arylcarboxamide, alkylthio or haloalkylthio; tyrosine, serine or threonine optionally substituted with alkyl or aryl; tryptophan, histidine, methionine, valine, norvaline, norleucine, octahydroindole-2-carboxylic acid; asparagine, glutamine, ornithine and lysine optionally substituted at the sidechain nitrogen atom with alkyl, alkenyl, alkynyl, alkoxyalkyl, alkylthioalkyl, alkylaminoalkyl, dialkylaminoalkyl, carboxyalkyl, alkoxycarbonyl alkyl or cycloalkyl, bicycloalkyl, cycloalkyl alkyl, bicycloalkyl alkyl or fused aryl-cycloalkyl alkyl optionally comprising 1 or more heteroatoms selected from N, O and S.

10. The method of claim 7 wherein R'₂ is H.

11. The method of claim 8 wherein R'₃ is H.

12. The method of claim 1 wherein AA₁ is Arg or an Arg mimetic.

13. The method of claim 1 wherein R₂ is alkyl or alkenyl substituted with guanidinyl, amino or amidylguanidine, benzyl optionally substituted with amidine; alkyl- or alkyl-amino pyridine; alkyl- or alkyl-aminoimidazole substituted with amino; or alkyl-cyclohexane optionally comprising nitrogen and optionally substituted with keto and amidine.

14. The method of claim 13 wherein R₂ is CH₂(CH₂)₂NHC(=NH)NH₂; —CH₂(CH₂)₄NH₂; benzylamidine-, —CH₂(CH₂)₂NH-pyridine; —CH₂NHC(O)NHC(=NH)NH₂; —CH₂CH₂CH₂-(imidazole)-NH₂; —CH₂CH₂NH-(imidazole)-NH₂; or —CH₂-(N,N-diketocyclohexane)-C(=NH)NH₂.

15. A method of claim 1 or 8 wherein said serine protease is tissue kallikrein.

16. A method of claim 15 wherein AA₁ is Arg or Arg mimetic, AA₅ is a bond from AA₄ to R₄, or a bond from AA₄ to R'₄, or separate bonds from AA₄ to R₄ and from AA₄ to R'₄, and AA₄, AA₃ and AA₂ are either an amino acid residue or an amino acid residue mimetic.

17. A method of claim 16 wherein AA₂ is Leu or Phe; and AA₃ is Arg or Arg mimetic, or Pro.

18. A method of claim 17 wherein AA₄ is Thr.

19. A method of claim 1 or 8 wherein said serine protease is a guanidinobenzoatase.

20. A method of claim 19 wherein AA₁ is Arg, Arg mimetic or guanidinobenzoyl.

21. A method of claim 1 or 8 wherein said serine protease is chymase.

22. A method of claim 21 wherein $AA_1$ is Tyr, Phe, Trp or Leu, $AA_2$, $AA_3$, $AA_4$ and $AA_5$ are an amino acid residue or an amino acid residue mimetic, and $R'_4$ is absent.

23. A method of claim 22 wherein $AA_2$ is Pro.

24. A method of claim 23 wherein $AA_3$ is His.

25. A method of claim 24 wherein $AA_4$ is Ile; and $AA_5$ is Tyr.

26. A method of claim 22 wherein $AA_2$ is a having one of the following structural formulas:

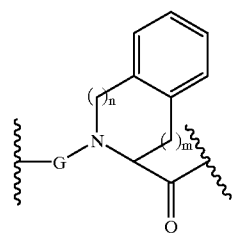
(IV)

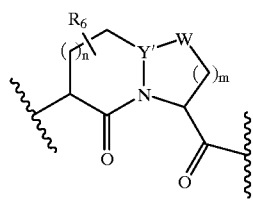
(V)

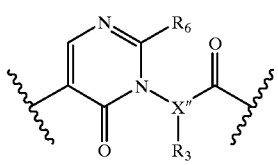
(VI)

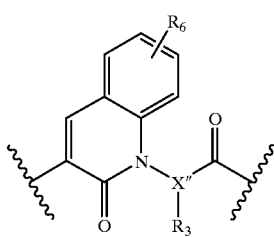
(VII)

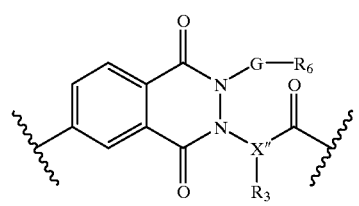
(VIII)

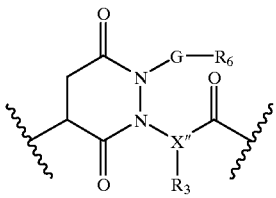
(IX)

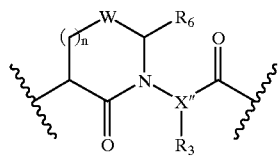
(X)

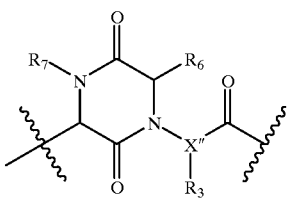
(XI)

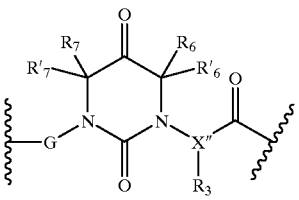
(XII)

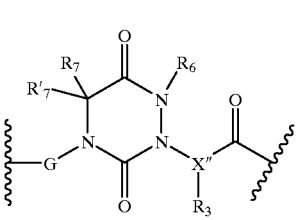
(XIII)

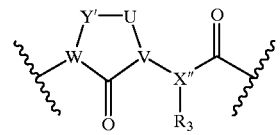
(XIV)

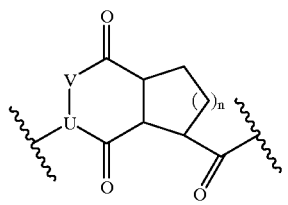
(XV)

(XVI)
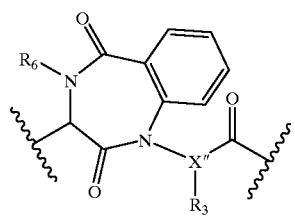

(XVII)
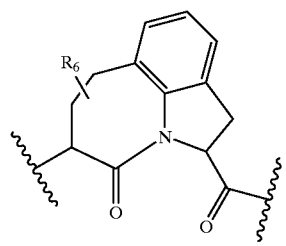

(XVIII)
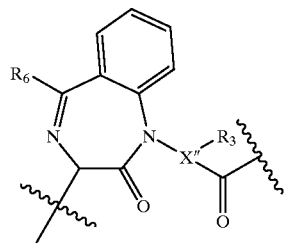

(XIX)
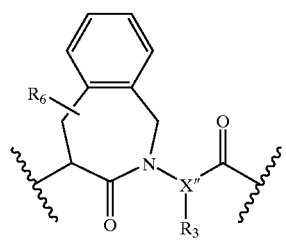

(XX)
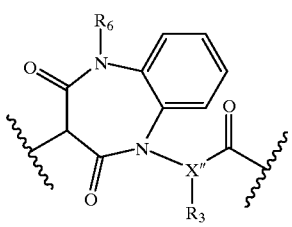

(XXI)
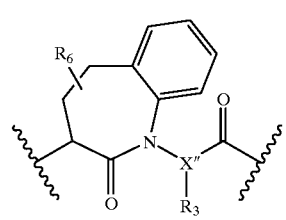

(XXII)
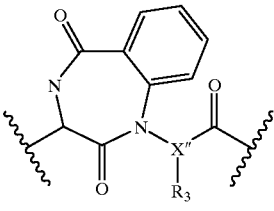

(XXIII)
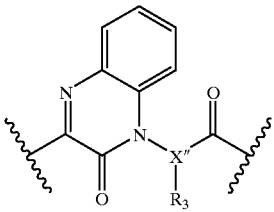

(XXIV)
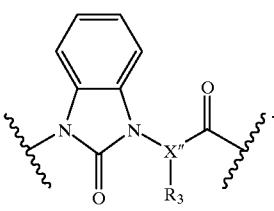

27. A method of claim 1 or 8 wherein said serine protease is mast cell tryptase.

28. A method of claim 27 wherein $AA_1$ is Arg or Arg mimetic, $AA_5$ and $AA_4$ together form a direct bond from $AA_3$ to $R_4$ and $R'_4$ is absent, and $AA_3$ and $AA_2$ are an amino acid residue or an amino acid residue mimetic.

29. A method of claim 28 wherein $AA_2$ is Gly, Val, Arg, Arg mimetic, Leu or Phe; and $AA_3$ is Leu, Arg, Arg mimetic, optionally substituted Lys or Ser, or Phe.

30. A method of claim 1 or 8 wherein said serine protease is prolyl oligopeptidase.

31. A method of claim 30 wherein $AA_1$ is Pro.

32. A method of claim 31 wherein $AA_2$ is Pro.

33. A method of claim 31 wherein the compound is N-[N-(4-phenyl-1-ketobutane)-(L)-prolyl]-2-(S)-[(5-(3-phenylpropane)-1,2,4-oxadiazolyl)-ketomethane]-pyrrolidine.

34. A method of claim 1 or 8 wherein said serine protease is hepatitis C virus NS3 polyprotein endopeptidase.

35. A method of claim 34 wherein $AA_1$ is Cys, $AA_5$ is a direct bond from $AA_4$ to $R_4$ and $R'_4$ is absent, and $AA_2$, $AA_3$ and $AA_4$ are an amino acid residue or an amino acid residue mimetic.

36. A method of claim 35 wherein $AA_2$ is Cys or Ala.

37. A method of claim 36 wherein $AA_3$ is Val.

38. A method of claim 37 wherein $AA_4$ is Val.

39. A method of claim 1 or 8 wherein said serine protease is human cytomegalovirus protease.

40. A method of claim 39 wherein $AA_1$ is Ala, $AA_5$ is a direct bond from $AA_4$ to $R_4$ and $R'_4$ is absent; $AA_4$ is an amino acid residue, an amino acid residue mimetic, or a direct bond; and $AA_3$ and $AA_2$ are an amino acid residue or an amino acid residue mimetic.

41. A method of claim 40 wherein $AA_2$ is optionally substituted Asn or Gln; Asp or Glu or an ester thereof, or optionally substituted Lys; and $AA_3$ is Val, Ile or Leu.

42. A method of claim 41 wherein $AA_4$ is Val or a direct bond.

43. A method of claim 1 or 8 wherein said serine protease is an assemblin.

44. A method of claim 43 wherein $AA_1$ is Ala, $AA_5$ is a direct bond from $AA_4$ to $R_4$ and $R'_4$ is absent; $AA_4$ is an amino acid residue, an amino acid residue mimetic, or a direct bond; and $AA_3$ and $AA_2$ are an amino acid residue or an amino acid residue mimetic.

45. A method of claim 44 wherein $AA_3$ is Leu, Val or Ile.

46. A method of claim 45 wherein $AA_4$ is optionally substituted Tyr or a direct bond.

47. A method of claim 46 wherein $AA_2$ is optionally substituted Gln or Lys.

48. A method of claim 1 or 8 wherein said serine protease is $\mu$-plasminogen activator.

49. The method of claim 47 wherein $AA_1$ is Arg, Arg mimetic or optionally substituted Lys; $AA_5$ is a direct bond to $R_4$ and $R'_4$ is absent; and $AA_2$, $AA_3$, and $AA_4$ are an amino acid residue or an amino acid residue mimetic.

50. A method of claim 49 wherein $AA_2$ is Gly; and $AA_3$ is optionally substituted Ser.

51. A method of claim 50 wherein $AA_4$ is Gly.

52. A method of claim 1 or 8 wherein said serine protease is t-plasminogen activator.

53. A method of 52 wherein $AA_1$ is Arg, Arg mimetic or optionally substituted Lys; $AA_5$ is a direct bond to $R_4$ and $R'_4$ is absent; and $AA_2$ and $AA_3$ are an amino acid residue or an amino acid residue mimetic.

54. A method of claim 53 wherein $AA_2$ is Gly or Ala; and $AA_3$ is Arg or Arg mimetic.

55. A method of claim 1 wherein said serine protease is Schistosoma serine protease.

56. A method of claim 1 or 8 wherein $AA_1$ is Arg, Arg mimetic, substituted or unsubstituted Lys, or Orn, and $AA_2$ is Phe.

57. A method of claim 56 wherein $AA_2$ is Phe.

58. A method of claim 57 wherein $AA_3$ is Pro.

59. The method of claim 1 wherein said method is effective to inhibit microbial growth.

60. The method of claim 1 or 56 wherein said method is effective to reduce perioperative blood loss.

61. The method of claim 1 wherein said method is effective to preserve transplantation tissues or organs.

62. The method of claim 1 wherein said method is effective to inhibit cancer cell growth or tumor progression or tumor metastasis or invasion.

63. The method of claim 1 wherein said method is effective to treat the symptoms associated with pulmonary vascular disease, restenosis or pulmonary hypertension myocarditis.

64. The method of claim 1 wherein said method is effective to treat the symptoms associated with bronchopulmonary dysplasia, myocardial necrosis or post-cardiac transplant coronary arteriopathy.

65. The method of claim 1 wherein said method is effective to treat the symptoms associated with atherosclerosis or reperfusion injury.

66. The method of claim 1 or 8 wherein said method is effective to treat the symptoms associated with Alzheimer's disease.

67. The method of claim 1 wherein said method is effective to treat the symptoms associated with hypoxia or ischemia.

68. The method of claim 1 wherein said method is effective to treat the symptoms associated with blood coagulation disorders.

69. N-[N-(4-phenyl-1-ketobutane)-(L)-prolyl]-2-(S)-[(5-(3-phenylpropane)-1,2,4-oxadiazolyl)-ketomethane]-pyrrolidine.

70. N-(Benzyloxycarbonyl)-L-valyl-N-[1-[3-[5-(3-trifluoromethylbenzyl)-1,2,4-oxadiazolyl]carbonyl]-2-(S)-methylpropyl]-N-benzylglycinamide;

N-Succinyl-L-valyl-N-[1-[3-[5-(3-trifluoromethylbenzyl)-1,2,4-oxadiazolyl]carbonyl]-2-phenylethylenyl]-L-prolinamide;

N-[4-(4-Morpholinylcarbonyl)benzoyl]-L-valyl-N-[1-[3-[5-(3-trifluoromethylbenzyl)-1,2,4-oxadiazolyl]carbonyl]-2-(S)-methylpropyl]-L-prolinamide; or N-Acetyl-L-alanyl-N-[1-[3-[5-(3-trifluoromethylbenzyl)-1,2,4-oxadiazolyl]carbonyl]-2-(S)-methylpropyl]-L-prolinamide.

71. N-(Benzyloxycarbonyl)-L-valyl-N-[1-[2-[5-(3-methylbenzyl)-1,3,4-oxadiazolyl]carbonyl]-1-methylethyl]-L-prolinamide;

N-(Benzyloxycarbonyl)-L-t-butylglycyl-N-[1-[3-[5-(3-trifluoromethylbenzyl)-1,2,4-oxadiazolyl]carbonyl]-2-methylpropyl]-L-prolinamide;

N-(Benzyloxycarbonyl)-L-Valyl-N-[1-[3-[5-(naphthyl-2-methylene)-1,2,4-oxadiazolyl]carbonyl]-2-(S)-methylpropyl]-L-prolinamide;

N-(Benzyloxycarbonyl)-L-TIC-N-[1-[2-[5-(3-methylbenzyl)-1,3,4-oxadiazolyl]carbonyl]-2-Methylpropyl]-L-Prolinamide;

N-(3-Pyridylcarbonyl)-L-Valyl-N-[1-[3-[5-(3-methylbenzyl)-1,3,4-oxadiazolyl]carbonyl]-2-(S)-Methylpropyl]-L-Prolinamide; or N-(Methanesulfonyl)-L-valyl-N-[1-[2-[5-(3-methylbenzyl)-1,3,4-oxadiazolyl]carbonyl]-2-(S)-methylpropyl]-L-prolinamide.

72. A method of inhibiting the enzymatic activity of a serine protease comprising contacting such protease with an inhibitory amount of a compound of formula (I):

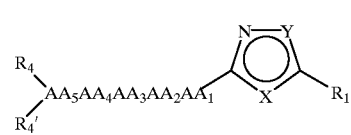

(I)

wherein $AA_2$, $AA_3$, $AA_4$ and $AA_5$ are independently an amino acid residue or amino acid residue mimetic, or a direct bond, and $AA_1$ is represented by formula (IIIc):

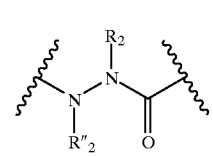

(IIIc)

and wherein $R_2$ and $R''_2$ are independently H; alkyl or alkenyl optionally substituted with 1–3 halo, hydroxy, thio, alkylthio, amino, alkylamino, dialkylamino, alkylguanidinyl, dialkylguanidinyl, guanidinyl or amidylguanidine; —RCOR', —RCOOR', —RNR'R"R° or —RC(O)NR'R" where R is alkyl or alkenyl, and R', R" and R° are independently H, alkyl, alkenyl, cycloalkyl or (C$_5$–C$_6$)aryl; or cycloalkyl, alkylcycloalkyl, alkenylcycloalkyl, alkyl-oxyaryl, alkyl-thioaryl, alkyl-aminoaryl, (C$_5$–C$_{12}$)aryl, (C$_5$–C$_{12}$)arylalkyl or (C$_5$–C$_{12}$) arylalkenyl optionally comprising 1–4 heteroatoms select from N, O and S, and optionally substituted with hydroxy, halo, cyano, keto, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, (C$_5$–C$_6$)aryl, —O-(C$_5$–C$_6$)aryl, arylcarboxamide, akylthio or haloalhylthio;

Y and X are independently O, S or N, said N being optionally substituted with (a) alkyl or alkenyl, which alkyl or alkenyl is optionally substituted with 1–3 halo atoms; or (b) (C$_5$–C$_6$)aryl, arylalkyl or arylalkenyl optionally comprising 1–3 heteroatoms selected from N, O and S, and optionally substituted with halo, cyano, nitro, hydroxy, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio;

R$_1$ is alkyl or alkenyl optionally substituted with 1–3 halo or hydroxy; alkylamino, dialkylamino, alkyldialkylamino; or cycloalkyl, alkylcycloalkyl, alkenylcycloalkyl, (C$_5$–C$_{12}$)aryl, (C$_5$–C$_{12}$)arylalkyl or (C$_5$–C$_{12}$)arylalkenyl optionally comprising 1–4 heteroatoms selected from N, O and S, and optionally substituted with halo, cyano, nitro, hydroxy, alkylenedioxy, haloalkyl, amino, aminoalkyl, dialkylamino, alkyl, alkenyl, alkynyl, alkoxy, haloalkoxy, carboxyl, carboalkoxy, alkylcarboxamide, (C$_5$–C$_6$)aryl, —O-(C$_5$–C$_6$)aryl, arylcarboxamide, alkylthio or haloalkylthio;

R$_4$ and R$_4$' are independently —C(O)R$_5$, —C(O)NHR$_5$, —S(O)$_2$R$_5$, —C(O)OR$_5$, —C(O)-(C$_5$–C$_6$)aryl-C(O)—R$_5$, —CH$_2$R$_5$ or R$_5$, where R$_5$ is H, alkyl, alkenyl or alkynyl optionally substituted with halo, cyano, nitro, hydroxy, alkoxy, haloalkyl, amino, aminoalkyl, dialkylamino, haloalkoxy, carboxyl, carboalkoxy or alkylcarboxamide; cycloalkyl, alkylcycloalkyl, (C$_5$–C$_{12}$)aryl or (C$_5$–C$_{12}$)arylalkyl optionally comprising 1–4 heteroatoms selected from N, O and S, and optionally substituted with halo, cyano, nitro, hydroxy, alkoxy, haloalkyl, amino, aminoalkyl, dialkylamino, haloalkoxy, carboxyl, carboalkoxy, alkylcarboxamide, alkyl, alkenyl, alkynyl or (C$_5$–C$_{12}$)aryl; or absent; or together R$_4$ and R$_4$' form a ring comprising 5–7 atoms selected from C, N, S and O; and wherein at least one of Y or X is N; or a pharmaceutically acceptable salt of any of the above.

73. The method of claim 72 wherein the serine protease is selected from the group consisting of elastase, chymotrypsin, cathespin G, trypsin, thrombin, plasma kallikrein, tissue kallikrein, guanidinobenzoatase, chymase, mast cell tryptase, pyrrolyl oligopeptidase, hepatitis C virus NS3 polyprotein endopeptidase, human cytomegalovirus protease, assemblin, μ-plasminogen activator, tissue plasminogen activator, and Schistosoma serine protease.

74. The method of claim 72 wherein the method is effective to inhibit microbial growth, reduce perioperative blood loss, preserve transplantation tissues or organs, inhibit cancer cell growth, tumor progression, or tumor metastasis; or ameliorate the symptoms associated with pulmonary vascular disease, restenosis, pulmonary hypertension myocarditis, bronchopulmonary dysplasia, myocardial necrosis, atherosclerosis, reperfusion injury, Alzheimer's disease, hypoxia, ischemia, or blood coagulation disorders.

75. The method of claim 72 wherein AA$_2$ is an amino acid residue, or of the formula (IIIb):

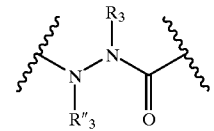

(IIIb)

or selected from a mimetic of formulas

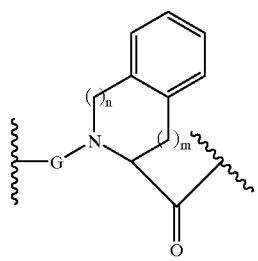

(IV)

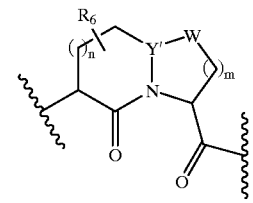

(V)

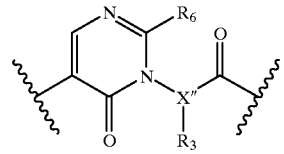

(VI)

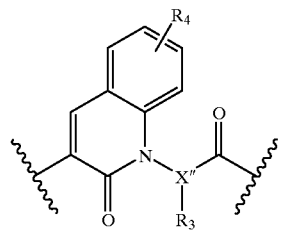

(VII)

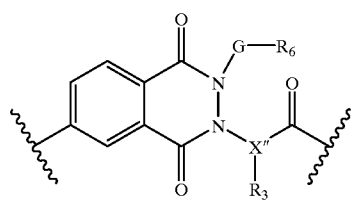

(VIII)

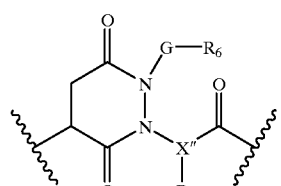 (IX)
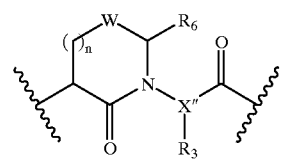 (X)
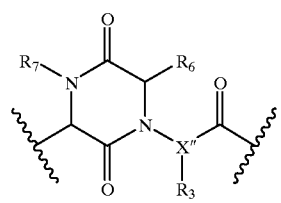 (XI)
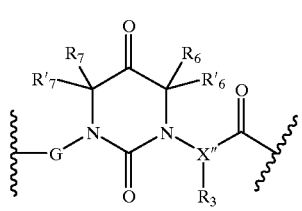 (XII)
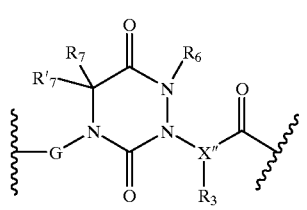 (XIII)
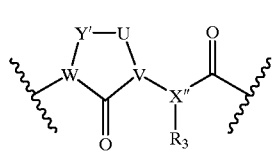 (XIV)
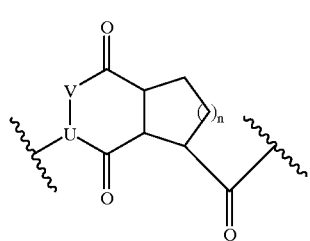 (XV)
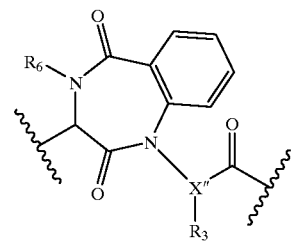 (XVI)
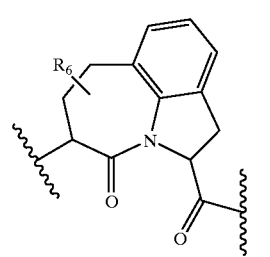 (XVII)
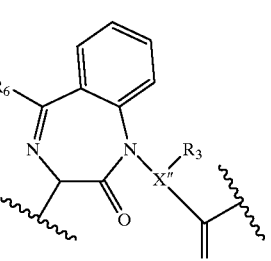 (XVIII)
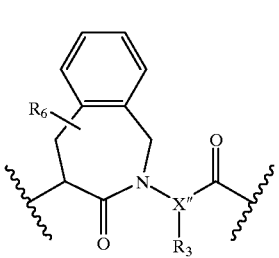 (XIX)
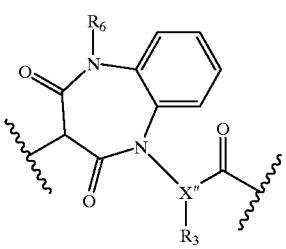 (XX)
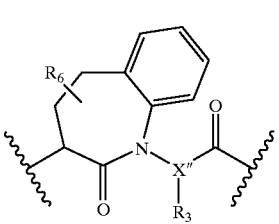 (XXI)

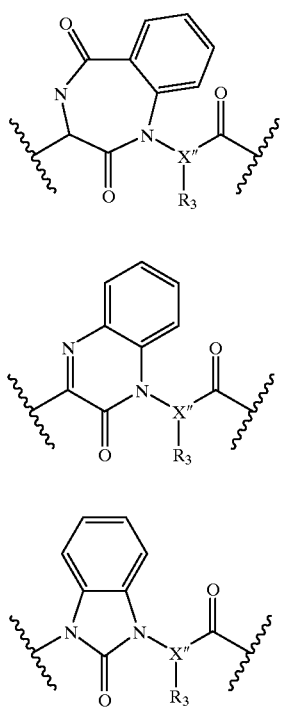

wherein X'' is N;

R₃ and R''₃ are independently H; alkyl or alkenyl optionally substituted with 1–3 halo, hydroxy, thio, alkylthio, amino, alkylamino, dialkylamino, alkylguanidinyl, dialkylguanidinyl, guanidinyl or amidylguanidine; —RCOR', —RCOOR', —RNR'R''R° or —RC(O)NR'R'' where R is alkyl or alkenyl, and R', R'' and R° are independently H, alkyl, alkenyl, cycloalkyl or (C₅–C₆)aryl; or cycloalkyl, alkylcycloalkyl, alkenylcycloalkyl, alkyl-oxyaryl, alkyl-thioaryl, alkyl-aminoaryl, (C₅–C₁₂)aryl, (C₅–C₁₂)arylalkyl or (C₅–C₁₂)arylalkenyl optionally comprising 1–4 heteroatoms selected from N, O and S, and optionally substituted with hydroxy, halo, cyano, keto, nitro, haloalkyl, amino, aminoalkyl, dialkylamino, amidine, alkylamidine, dialkylamidine, alkyl, alkenyl, alkynyl, alkoxy, haloalkoxy, carboxyl, carboalkoxy, alkylcarboxamide, (C₅–C₆)aryl, —O-(C₅–C₆)aryl, arylcarboxamide, alkylthio or haloalkylthio;

m is 0, 1 or 2;

n is 0, 1 or 2,

G is —C(O)—, —NHC(O)—, —S(O)₂—, —OC(O)—, —CH₂— or a direct bond;

R₆, R₇, R'₆, R'₇ are independently H, alkyl, alkenyl, halo, alkoxy, carboxyl, carboalkoxy, amino, aminoalkyl, dialkylamino; cycloalkyl, (C₅–C₆)aryl or (C₅–C₆) arylalkyl optionally comprising 1–3 heteroatoms selected from N, O and S, and optionally substituted with alkyl, alkenyl, alkynyl, halo, cyano, nitro, hydroxy, haloalkyl, amino, alkylamino, dialkylamino, alkoxy, haloalkoxy, carboxyl, carboalkoxy, alkylcarboxamide, alkylthio, guanidine, alkylguanidine, dialkylguanidine, amidine, alkylamidine or dialkylamidine; and U, V, W and Y' are independently or together N, C, C(O), N(R₉) where R₉ is H, alkyl, halo, alkoxy, carboalkoxy, cycloalkoxy, carboxyl, alkylthio, amino, alkylamino, dialkylamino, or aryl, fused aryl or cycloalkyl optionally comprising 1 or more heteroatoms selected from O, S and N, and optionally substituted with halo or alkyl; N(R₁₀) where R₁₀ is H, alkyl, alkenyl or cycloalkyl, aryl, arylalkyl or fused aryl-cycloalkyl optionally comprising 1–4 heteroatoms selected from N, O and S, and optionally substituted with alkyl, alkenyl, alkynyl, halo, cyano, nitro, haloalkyl, hydroxy, amino, alkylamino, dialkylamino, alkoxy, haloalkoxy, carboxyl, carboalkoxy, alkylcarboxamide, alkylthio, guanidine, alkylguanidine, dialkylguanidine, amidine, alkylamidine or dialkylamidine; or C(R₁₁)(R₁₂) where R₁₁ and R₁₂ are independently or together H, alkyl, alkylthioalkyl or cycloalkyl, alkylcycloalkyl, phenyl or phenyl alkyl optionally substituted with guanidine, carboalkoxy, hydroxy, haloalkyl, alkylthio, alkylguanidine, dialkylguanidine, amidine, alkylamidine or dialkylamidine.

76. The method of claim 58 wherein said method is effective to preserve transplantation tissues or organs.

77. N-(Phenylsulfonyl)-L-valyl-N-[1-[2-[5-(3-methylbenzyl)-1,3,4-oxadiazolyl]carbonyl]-2-(S)-methylpropyl]-L-prolinamide;

N-(3-Pyridylcarbonyl)-L-valyl-N-[1-[3-[5-(3-trifluoromethylbenzyl)-1,2,4-oxadiazolyl]carbonyl]-2-(S)-methylpropyl]-L-prolinamide;

N-(4-Pyridylmethyleneoxycarbonyl)-L-valyl-N-[1-[3-[5-(3-trifluoromethylbenzyl)-1,2,4-oxadiazolyl]carbonyl]-2-(S)-methylpropyl]-L-prolinamide;

N-(4-Pyridylmethyleneoxycarbonyl)-L-valyl-N-[1-[2-[5-(3-methylbenzyl)-1,3,4-oxadiazolyl]carbonyl]-2-(S)-methylpropyl]-L-prolinamide; or N-(Pyrrolyl-2-carbonyl)-L-valyl-N-[1-[2-[5-(3-methylbenzyl)-1,3,4-oxadiazolyl]carbonyl]-2-(S)-methylpropyl]-N-(1-indanyl)glycinamide.

* * * * *

SEQUENCE LISTING
<160> NUMBER OF SEQ ID NOS: 58
<210> SEQ ID NO 1
<211> LENGTH: 4

```
<212> TYPE: PRT
<213> ORGANISM: Serine Protease

<400> SEQUENCE: 1

Thr Arg Leu Arg
 1

<210> SEQ ID NO 2
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 2

Thr Arg Leu Xaa
 1

<210> SEQ ID NO 3
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 3

Thr Xaa Leu Arg
 1

<210> SEQ ID NO 4
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 4

Thr Xaa Leu Xaa
 1

<210> SEQ ID NO 5
<211> LENGTH: 4
<212> TYPE: PRT
<213> ORGANISM: Serine Protease

<400> SEQUENCE: 5

Thr Pro Leu Arg
 1

<210> SEQ ID NO 6
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 6

Thr Pro Leu Xaa
 1
```

```
<210> SEQ ID NO 7
<211> LENGTH: 4
<212> TYPE: PRT
<213> ORGANISM: Serine Protease

<400> SEQUENCE: 7

Thr Arg Phe Arg
 1

<210> SEQ ID NO 8
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 8

Thr Arg Phe Xaa
 1

<210> SEQ ID NO 9
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 9

Thr Xaa Phe Arg
 1

<210> SEQ ID NO 10
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 10

Thr Xaa Phe Xaa
 1

<210> SEQ ID NO 11
<211> LENGTH: 4
<212> TYPE: PRT
<213> ORGANISM: Serine Protease

<400> SEQUENCE: 11

Thr Pro Phe Arg
 1

<210> SEQ ID NO 12
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic
```

```
<400> SEQUENCE: 12

Thr Pro Phe Xaa
 1

<210> SEQ ID NO 13
<211> LENGTH: 5
<212> TYPE: PRT
<213> ORGANISM: Serine Protease

<400> SEQUENCE: 13

Tyr Ile His Pro Tyr
 1               5

<210> SEQ ID NO 14
<211> LENGTH: 5
<212> TYPE: PRT
<213> ORGANISM: Serine Protease

<400> SEQUENCE: 14

Tyr Ile His Pro Phe
 1               5

<210> SEQ ID NO 15
<211> LENGTH: 5
<212> TYPE: PRT
<213> ORGANISM: Serine Protease

<400> SEQUENCE: 15

Tyr Ile His Pro Trp
 1               5

<210> SEQ ID NO 16
<211> LENGTH: 5
<212> TYPE: PRT
<213> ORGANISM: Serine Protease

<400> SEQUENCE: 16

Tyr Ile His Pro Leu
 1               5

<210> SEQ ID NO 17
<211> LENGTH: 5
<212> TYPE: PRT
<213> ORGANISM: Serine Protease
<220> FEATURE:
<221> NAME/KEY: VARIANT
<222> LOCATION: (1)...(5)
<223> OTHER INFORMATION: Xaa =Mimetic of formulas IV to XXIV

<400> SEQUENCE: 17

Tyr Ile His Xaa Leu
 1               5

<210> SEQ ID NO 18
<211> LENGTH: 4
<212> TYPE: PRT
<213> ORGANISM: Serine Protease

<400> SEQUENCE: 18

Val Val Ala Cys
 1

<210> SEQ ID NO 19
<211> LENGTH: 4
```

```
<212> TYPE: PRT
<213> ORGANISM: Serine Protease

<400> SEQUENCE: 19

Val Val Cys Cys
 1

<210> SEQ ID NO 20
<211> LENGTH: 4
<212> TYPE: PRT
<213> ORGANISM: Serine Protease

<400> SEQUENCE: 20

Val Val Asn Ala
 1

<210> SEQ ID NO 21
<211> LENGTH: 4
<212> TYPE: PRT
<213> ORGANISM: Serine Protease

<400> SEQUENCE: 21

Val Ile Asn Ala
 1

<210> SEQ ID NO 22
<211> LENGTH: 4
<212> TYPE: PRT
<213> ORGANISM: Serine Protease

<400> SEQUENCE: 22

Val Leu Asn Ala
 1

<210> SEQ ID NO 23
<211> LENGTH: 4
<212> TYPE: PRT
<213> ORGANISM: Serine Protease

<400> SEQUENCE: 23

Val Val Asp Ala
 1

<210> SEQ ID NO 24
<211> LENGTH: 4
<212> TYPE: PRT
<213> ORGANISM: Serine Protease

<400> SEQUENCE: 24

Val Ile Asp Ala
 1

<210> SEQ ID NO 25
<211> LENGTH: 4
<212> TYPE: PRT
<213> ORGANISM: Serine Protease

<400> SEQUENCE: 25

Val Leu Asp Ala
 1

<210> SEQ ID NO 26
<211> LENGTH: 4
<212> TYPE: PRT
<213> ORGANISM: Serine Protease
```

```
<400> SEQUENCE: 26

Val Val Gln Ala
1

<210> SEQ ID NO 27
<211> LENGTH: 4
<212> TYPE: PRT
<213> ORGANISM: Serine Protease

<400> SEQUENCE: 27

Val Ile Gln Ala
1

<210> SEQ ID NO 28
<211> LENGTH: 4
<212> TYPE: PRT
<213> ORGANISM: Serine Protease

<400> SEQUENCE: 28

Val Leu Gln Ala
1

<210> SEQ ID NO 29
<211> LENGTH: 4
<212> TYPE: PRT
<213> ORGANISM: Serine Protease

<400> SEQUENCE: 29

Val Val Glu Ala
1

<210> SEQ ID NO 30
<211> LENGTH: 4
<212> TYPE: PRT
<213> ORGANISM: Serine Protease

<400> SEQUENCE: 30

Val Ile Glu Ala
1

<210> SEQ ID NO 31
<211> LENGTH: 4
<212> TYPE: PRT
<213> ORGANISM: Serine Protease

<400> SEQUENCE: 31

Val Leu Glu Ala
1

<210> SEQ ID NO 32
<211> LENGTH: 4
<212> TYPE: PRT
<213> ORGANISM: Serine Protease

<400> SEQUENCE: 32

Val Val Lys Ala
1

<210> SEQ ID NO 33
<211> LENGTH: 4
<212> TYPE: PRT
<213> ORGANISM: Serine Protease
```

```
<400> SEQUENCE: 33

Val Ile Lys Ala
1

<210> SEQ ID NO 34
<211> LENGTH: 4
<212> TYPE: PRT
<213> ORGANISM: Serine Protease

<400> SEQUENCE: 34

Val Leu Lys Ala
1

<210> SEQ ID NO 35
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = A derivative or ester of Asn, Asp, Gln,
                        Glu or Lys

<400> SEQUENCE: 35

Val Val Xaa Ala
1

<210> SEQ ID NO 36
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = A derivative or ester of Asn, Asp, Gln,
                        Glu or Lys

<400> SEQUENCE: 36

Val Ile Xaa Ala
1

<210> SEQ ID NO 37
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = A derivative or ester of Asn, Asp, Gln,
                        Glu or Lys

<400> SEQUENCE: 37

Val Leu Xaa Ala
1

<210> SEQ ID NO 38
<211> LENGTH: 4
<212> TYPE: PRT
<213> ORGANISM: Serine Protease

<400> SEQUENCE: 38

Tyr Leu Gln Ala
1

<210> SEQ ID NO 39
<211> LENGTH: 4
```

```
<212> TYPE: PRT
<213> ORGANISM: Serine Protease

<400> SEQUENCE: 39

Tyr Val Gln Ala
 1

<210> SEQ ID NO 40
<211> LENGTH: 4
<212> TYPE: PRT
<213> ORGANISM: Serine Protease

<400> SEQUENCE: 40

Tyr Ile Gln Ala
 1

<210> SEQ ID NO 41
<211> LENGTH: 4
<212> TYPE: PRT
<213> ORGANISM: Serine Protease

<400> SEQUENCE: 41

Tyr Leu Lys Ala
 1

<210> SEQ ID NO 42
<211> LENGTH: 4
<212> TYPE: PRT
<213> ORGANISM: Serine Protease

<400> SEQUENCE: 42

Tyr Val Lys Ala
 1

<210> SEQ ID NO 43
<211> LENGTH: 4
<212> TYPE: PRT
<213> ORGANISM: Serine Protease

<400> SEQUENCE: 43

Tyr Ile Lys Ala
 1

<210> SEQ ID NO 44
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = A derivative of Gln or Lys

<400> SEQUENCE: 44

Tyr Leu Xaa Ala
 1

<210> SEQ ID NO 45
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = A derivative of Gln or Lys
```

```
<400> SEQUENCE: 45

Tyr Val Xaa Ala
 1

<210> SEQ ID NO 46
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = A derivative of Gln or Lys

<400> SEQUENCE: 46

Tyr Ile Xaa Ala
 1

<210> SEQ ID NO 47
<211> LENGTH: 4
<212> TYPE: PRT
<213> ORGANISM: Serine Protease

<400> SEQUENCE: 47

Gly Ser Arg Arg
 1

<210> SEQ ID NO 48
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 48

Gly Ser Arg Xaa
 1

<210> SEQ ID NO 49
<211> LENGTH: 4
<212> TYPE: PRT
<213> ORGANISM: Serine Protease

<400> SEQUENCE: 49

Gly Ser Arg Lys
 1

<210> SEQ ID NO 50
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic or Lys derivative

<400> SEQUENCE: 50

Gly Ser Xaa Arg
 1

<210> SEQ ID NO 51
<211> LENGTH: 4
<212> TYPE: PRT
<213> ORGANISM: Serine Protease
<220> FEATURE:
<221> NAME/KEY: VARIANT
```

```
<222> LOCATION: (3)...(3)
<223> OTHER INFORMATION: Xaa = Arg mimetic or Lys derivative
<220> FEATURE:
<221> NAME/KEY: VARIANT
<222> LOCATION: (4)...(4)
<223> OTHER INFORMATION: Xaa = Arg mimetic

<400> SEQUENCE: 51

Gly Ser Xaa Xaa
 1

<210> SEQ ID NO 52
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic or Lys derivative

<400> SEQUENCE: 52

Gly Ser Xaa Lys
 1

<210> SEQ ID NO 53
<211> LENGTH: 4
<212> TYPE: PRT
<213> ORGANISM: Serine Protease

<400> SEQUENCE: 53

Gly Ser Lys Arg
 1

<210> SEQ ID NO 54
<211> LENGTH: 4
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 54

Gly Ser Lys Xaa
 1

<210> SEQ ID NO 55
<211> LENGTH: 4
<212> TYPE: PRT
<213> ORGANISM: Serine Protease

<400> SEQUENCE: 55

Gly Ser Lys Lys
 1

<210> SEQ ID NO 56
<211> LENGTH: 4
<212> TYPE: PRT
<213> ORGANISM: Serine Protease

<400> SEQUENCE: 56

Gly Ser Gly Arg
 1

<210> SEQ ID NO 57
<211> LENGTH: 4
```

```
<212> TYPE: PRT
<213> ORGANISM: Serine Protease
<220> FEATURE:
<221> NAME/KEY: VARIANT
<222> LOCATION: (1)...(4)
<223> OTHER INFORMATION: Xaa = Arg mimetic

<400> SEQUENCE: 57

Gly Ser Gly Xaa
 1

<210> SEQ ID NO 58
<211> LENGTH: 4
<212> TYPE: PRT
<213> ORGANISM: Serine Protease

<400> SEQUENCE: 58

Gly Ser Gly Lys
```